(12) United States Patent
Wagner et al.

(10) Patent No.: US 8,936,647 B2
(45) Date of Patent: Jan. 20, 2015

(54) ELBOW PROSTHESIS

(71) Applicant: Zimmer, Inc., Warsaw, IN (US)

(72) Inventors: Terry W. Wagner, Mishawaka, IN (US);
Brian L. Kincaid, Warsaw, IN (US);
Kenton A. Walz, Fort Wayne, IN (US);
Stephen H. Hoag, Warsaw, IN (US);
Mark Reed Marqueling, Chururbusco, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 13/800,567

(22) Filed: Mar. 13, 2013

(65) Prior Publication Data

US 2013/0345818 A1 Dec. 26, 2013

Related U.S. Application Data

(60) Provisional application No. 61/663,452, filed on Jun. 22, 2012.

(51) Int. Cl.
*A61F 2/38* (2006.01)
*A61F 2/30* (2006.01)

(52) U.S. Cl.
CPC ............... *A61F 2/3804* (2013.01); *A61F 2/384* (2013.01); *A61F 2002/3813* (2013.01); *A61F 2002/30382* (2013.01); *A61F 2002/30507* (2013.01); *A61F 2002/30632* (2013.01)
USPC .................... 623/20.11; 623/20.12; 623/20.13

(58) Field of Classification Search
CPC .................................................... A61F 2/3804
USPC ...................... 623/19.11–20.15, 21.11–21.17
IPC ......................................................... A61F 2/38
See application file for complete search history.

(56) References Cited

U.S. PATENT DOCUMENTS

| 750,678 | A | 1/1904 | Morton |
| 1,110,528 | A | 9/1914 | Borresen |

(Continued)

FOREIGN PATENT DOCUMENTS

| FR | 2575384 A1 | 7/1986 |
| FR | 2579454 A1 | 10/1986 |

(Continued)

OTHER PUBLICATIONS

"U.S. Appl. No. 12/856,112, Examiner Interview Summary mailed Jul. 11, 2013", 3 pgs.

(Continued)

*Primary Examiner* — Yashita Sharma
(74) *Attorney, Agent, or Firm* — Schwegman Lundberg & Woessner, P.A.

(57) ABSTRACT

An elbow prosthesis can include a humeral component having a yoke, an ulnar component having a head, a humeral bearing positionable in a base of the humeral component, an ulnar bearing assembly configured to engage with the head, and a pin extendable through the bearing assembly and the head. The pin can be extendable into first and second ears of the yoke to enable pivotable movement of the ulnar component relative to the humeral component. The elbow prosthesis can include a first fastener insertable through the first ear of the yoke and configured to engage with the pin, and a second fastener insertable through the second ear of the yoke and configured to engage with the pin.

22 Claims, 18 Drawing Sheets

(56) References Cited

U.S. PATENT DOCUMENTS

| | | | |
|---|---|---|---|
| 1,517,162 A | 11/1924 | King |
| 1,677,365 A | 7/1928 | Peck |
| 2,462,536 A | 2/1949 | Muter |
| 2,737,917 A | 3/1956 | Steele |
| 2,837,951 A | 6/1958 | Phelps |
| 3,157,075 A | 11/1964 | Filia |
| 3,187,751 A | 6/1965 | Coren |
| 3,563,124 A | 2/1971 | Gargrave |
| 3,641,652 A | 2/1972 | Arnold et al. |
| 3,708,805 A | 1/1973 | Scales et al. |
| 3,816,854 A | 6/1974 | Schlein |
| 3,826,160 A | 7/1974 | Allen et al. |
| 4,038,704 A | 8/1977 | Ring |
| 4,227,299 A | 10/1980 | Kuehling |
| 4,280,231 A | 7/1981 | Swanson |
| 4,306,550 A | 12/1981 | Forte |
| 4,365,411 A | 12/1982 | Muldoon |
| 4,383,337 A | 5/1983 | Volz et al. |
| 4,420,879 A | 12/1983 | Harringer |
| 4,587,964 A | 5/1986 | Walker et al. |
| 4,765,328 A | 8/1988 | Keller et al. |
| 4,822,364 A | 4/1989 | Inglis et al. |
| 4,982,631 A | 1/1991 | Lowther |
| 5,020,399 A | 6/1991 | Annis et al. |
| 5,061,271 A | 10/1991 | Van Zile |
| 5,197,368 A | 3/1993 | Meyer et al. |
| 5,314,479 A | 5/1994 | Rockwood, Jr. et al. |
| 5,376,121 A | 12/1994 | Huene et al. |
| 5,702,457 A | 12/1997 | Walch et al. |
| 5,702,486 A | 12/1997 | Craig et al. |
| 5,723,015 A | 3/1998 | Risung et al. |
| 5,961,555 A | 10/1999 | Hubner |
| 6,027,534 A | 2/2000 | Wack et al. |
| 6,102,953 A | 8/2000 | Huebner |
| 6,129,764 A | 10/2000 | Servidio |
| 6,168,630 B1 | 1/2001 | Keller et al. |
| 6,197,063 B1 | 3/2001 | Dews |
| 6,290,725 B1 | 9/2001 | Weiss et al. |
| 6,314,843 B1 | 11/2001 | Wiebe et al. |
| 6,379,387 B1 | 4/2002 | Tornier |
| 6,673,114 B2 | 1/2004 | Hartdegen et al. |
| 6,699,290 B1 | 3/2004 | Wack et al. |
| 6,716,248 B2 * | 4/2004 | Huene | 623/20.12 |
| 6,739,068 B1 | 5/2004 | Rinner |
| 6,767,368 B2 | 7/2004 | Tornier |
| 6,890,357 B2 | 5/2005 | Tornier |
| 6,923,832 B1 * | 8/2005 | Sharkey et al. | 623/20.34 |
| 6,964,088 B2 | 11/2005 | Crevoisier |
| 6,969,407 B2 | 11/2005 | Klotz et al. |
| 7,097,663 B1 | 8/2006 | Nicol et al. |
| 7,247,170 B2 | 7/2007 | Graham et al. |
| 7,338,528 B2 | 3/2008 | Stone et al. |
| 7,604,666 B2 | 10/2009 | Berelsman et al. |
| 7,625,406 B2 | 12/2009 | Berelsman et al. |
| 7,722,625 B2 | 5/2010 | Sanders et al. |
| 7,846,376 B2 | 12/2010 | Abt et al. |
| 7,850,737 B2 | 12/2010 | Morrey |
| 8,328,873 B2 * | 12/2012 | Metzger et al. | 623/20.28 |
| 2001/0021876 A1 | 9/2001 | Terrill-Grisoni et al. |
| 2002/0156534 A1 | 10/2002 | Grusin et al. |
| 2002/0165614 A1 | 11/2002 | Tornier |
| 2003/0144739 A1 | 7/2003 | Huene |
| 2003/0208277 A1 | 11/2003 | Weiss et al. |
| 2004/0186581 A1 | 9/2004 | Huene |
| 2004/0193268 A1 | 9/2004 | Hazebrouck |
| 2004/0193276 A1 | 9/2004 | Maroney et al. |
| 2004/0243243 A1 | 12/2004 | Tornier |
| 2005/0043806 A1 | 2/2005 | Cook et al. |
| 2005/0075735 A1 | 4/2005 | Berelsman et al. |
| 2006/0100712 A1 | 5/2006 | Ball |
| 2006/0100713 A1 | 5/2006 | Ball |
| 2006/0111788 A1 | 5/2006 | Ball |
| 2006/0111789 A1 | 5/2006 | Ball |
| 2006/0173546 A1 | 8/2006 | Berelsman et al. |
| 2006/0224243 A1 | 10/2006 | Pare et al. |
| 2006/0247786 A1 | 11/2006 | Ball |
| 2007/0129808 A1 | 6/2007 | Justin et al. |
| 2007/0282450 A1 | 12/2007 | Habermeyer et al. |
| 2007/0299527 A1 | 12/2007 | Mccleary et al. |
| 2008/0015706 A1 | 1/2008 | Berelsman et al. |
| 2008/0033566 A1 | 2/2008 | Berelsman et al. |
| 2008/0114461 A1 | 5/2008 | Collazo |
| 2008/0306601 A1 | 12/2008 | Dreyfuss |
| 2009/0024221 A1 | 1/2009 | Ball |
| 2009/0105839 A1 | 4/2009 | Ikegami et al. |
| 2010/0051141 A1 | 3/2010 | Bhambri |
| 2010/0087928 A1 | 4/2010 | Graham et al. |
| 2010/0160985 A1 | 6/2010 | Pannu |
| 2010/0179661 A1 | 7/2010 | Berelsman et al. |
| 2010/0222887 A1 | 9/2010 | Katrana et al. |
| 2011/0125274 A1 | 5/2011 | Bartel et al. |
| 2011/0153024 A1 | 6/2011 | Wagner et al. |
| 2011/0172781 A1 | 7/2011 | Katrana et al. |
| 2012/0000326 A1 | 1/2012 | Sheriff |
| 2012/0095473 A1 | 4/2012 | Soliman et al. |
| 2013/0340236 A1 | 12/2013 | Wagner et al. |

FOREIGN PATENT DOCUMENTS

| | | |
|---|---|---|
| FR | 2660857 B1 | 12/1997 |
| WO | WO-8904238 A1 | 5/1989 |
| WO | WO-9725943 A1 | 7/1997 |
| WO | WO-2006129495 A1 | 12/2006 |
| WO | WO-2008002545 A2 | 1/2008 |
| WO | WO-2010098791 A2 | 9/2010 |
| WO | WO-2011060430 A2 | 5/2011 |
| WO | WO-2013192408 A1 | 12/2013 |

OTHER PUBLICATIONS

"U.S. Appl. No. 12/856,112, Examiner Interview Summary mailed Dec. 17, 2012", 5 pgs.

"U.S. Appl. No. 12/856,112, Final Office Action mailed Apr. 26, 2013", 9 pgs.

"U.S. Appl. No. 12/856,112, Non Final Office Action mailed May 30, 2012", 11 pgs.

"U.S. Appl. No. 12/856,112, Response filed May 14, 2012 to Restriction Requirement mailed Apr. 13, 2012", 9 pgs.

"U.S. Appl. No. 12/856,112, Response filed Jul. 1, 2013 to Final Office Action mailed Apr. 26, 2013", 12 pgs.

"U.S. Appl. No. 12/856,112, Response filed Nov. 30, 2012 to Non Final Office Action mailed May 30, 2012", 18 pgs.

"U.S. Appl. No. 12/856,112, Restriction Requirement mailed Apr. 13, 2012", 7 pgs.

"The Ball Lock System—Dayton True Position Retainers", Brochure; Dayton Progress Corporation, (2002), 6 pgs.

"Zimmer Coonrad/Morrey Total Elbow Arthroplastly—Impaction Grafting Procedure", Surgical Technique for Revision; Zimmer, Inc., (2002), 2 pgs.

"Zimmer Coonrad/Morrey Total Elbow, Interchangeability, Anterior Flange, Clinical History", Surgical Technique; 97-8106-102-00 Rev. 2, Zimmer, Inc., (2002, 2005, 2009), 11 pgs.

"Zimmer Coonrad/Morrey Total Elbow, Interchangeability, Anterior Flange, Clinical Success", Brochure; 97-8106-301-00 Zimmer, Inc., (2000, 2006, 2007), 4 pgs.

"U.S. Appl. No. 12/856,112, Advisory Action mailed Aug. 15, 2013", 3 pgs.

"U.S. Appl. No. 12/856,112, Response filed Aug. 23, 2013 to Final Office Action mailed Apr. 26, 2013 and Advisory Action mailed Aug. 15, 2013", 12 pgs.

"U.S. Appl. No. 13/800,650, Preliminary Amendment filed Aug. 8, 2013", 7 pgs.

"International Application Serial No. PCT/US2013/046792, International Search Report mailed Aug. 23, 2013", 6 pgs.

"International Application Serial No. PCT/US2013/046792, Written Opinion mailed Aug. 23, 2013", 7 pgs.

"U.S. Appl. No. 12/856,112, Non Final Office Action mailed Mar. 14, 2014", 10 pgs.

\* cited by examiner

ELBOW PROSTHESIS

CROSS-REFERENCE TO RELATED APPLICATION(S)

This application claims the benefit of priority under 35 U.S.C. §119(e) of Wagner et al., U.S. Provisional Patent Application Ser. No. 61/663,452, entitled "MODULAR ELBOW PROSTHESIS," filed on Jun. 22, 2012, which is herein incorporated by reference in its entirety.

This application is related to U.S. Ser. No. 13/800,650, filed on the same day as this application, entitled "ASSEMBLY TOOL FOR A PROSTHESIS."

TECHNICAL FIELD

The present patent application relates to an orthopedic prosthesis and, more particularly, to an apparatus and methods for an elbow prosthesis.

BACKGROUND

A joint arthroplasty procedure may be performed to repair or replace damaged bone of a patient's joint, such as bone that is damaged due to a traumatic injury or a degenerative illness. For example, during a total elbow arthroplasty procedure, the surgeon implants a prosthetic humeral component into the distal end of a patient's humerus and a prosthetic ulnar component into the proximal end of the patient's ulna. The prosthetic humeral component and the prosthetic ulnar component are generally joined by a hinge that enables pivoting movement between the prosthetic humeral component and the prosthetic ulnar component, to recreate the natural, anatomical articulation of the elbow joint.

Overview

The present inventors recognize, among other things, an opportunity for an elbow prosthesis that allows for articulation of an ulnar component relative to a humeral component, while minimizing movement of the supporting components of the elbow prosthesis, including the bearing components and fasteners used to secure the components of the elbow prosthesis. The elbow prosthesis described herein can be used, for example, in a primary total elbow arthroplasty procedure or in a revision procedure.

To better illustrate the elbow prosthesis and methods disclosed herein, the following non-limiting examples are provided:

In an example, an elbow prosthesis comprises a humeral component comprising a humeral stem and a yoke having first and second ears extending from a base of the yoke, a humeral bearing positionable in the base of the yoke, an ulnar component comprising an ulnar stem and an ulnar head, a first ulnar bearing positionable between the first ear of the yoke and the ulnar head, a second ulnar being positionable between the second ear of the yoke and the ulnar head, a pin having a first end portion and a second end portion and configured to extend through the ulnar head, the first ulnar bearing and the second ulnar bearing, a first fastener insertable through at least a portion of the first ear of the yoke for engaging with the first end portion of the pin, and a second fastener insertable through at least a portion of the second ear of the yoke for engaging with the second end portion of the pin. The first end portion of the pin can be configured to extend into the first ear of the yoke and the second end portion of the pin can be configured to extend into the second ear of the yoke. The ulnar component can be configured to pivot about the pin to enable movement of the ulnar component relative to the humeral component.

In an example, an elbow prosthesis comprises a humeral component comprising a humeral stem and a yoke having first and second ears extending from a base of the yoke, an ulnar component comprising an ulnar stem and an ulnar head, an ulnar bearing assembly structured to engage the ulnar head, a pin configured to extend through the ulnar head and the bearing assembly, a first screw having a threaded head configured to be received within the threaded bore of the first ear, and a second screw having a threaded head configured to be received within the threaded bore of the second ear. Each of the first and second ears of the yoke can have a threaded bore. The pin can have a first end portion positionable within a first opening in the first ear of the yoke and a second end portion positionable within a second opening in the second ear of the yoke. The ulnar component can be configured to pivot about the pin to enable movement of the ulnar component relative to the humeral component. The first screw can include a non-threaded portion configured to engage with the first end portion of the pin. The second screw can include a non-threaded portion configured to engage with the second end portion of the pin.

In an example, a method of repairing an elbow joint of a patient comprises inserting an ulnar stem of an ulnar component into an ulnar medullary canal of the patient, assembling a bearing assembly onto an ulnar head of the ulnar component, inserting a humeral stem of a humeral component into a humeral medullary canal of the patient, placing a first end portion of a pin into a first opening in a first ear of the yoke and a second end portion of the pin into a second opening in a second ear of the yoke, and threading a first fastener into the first ear of the yoke and a second fastener into the second ear of the yoke to secure the humeral component to the ulnar component. The ulnar head of the ulnar component can remain exposed outside of the ulnar medullary canal. A yoke of the humeral component can remain exposed outside of the humeral medullary canal. The ulnar component can pivot relative to the humeral component. A portion of the first fastener can engage with a first end portion of the pin and a portion of the second fastener can engage with a second end portion of the pin.

This overview is intended to provide a summary of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
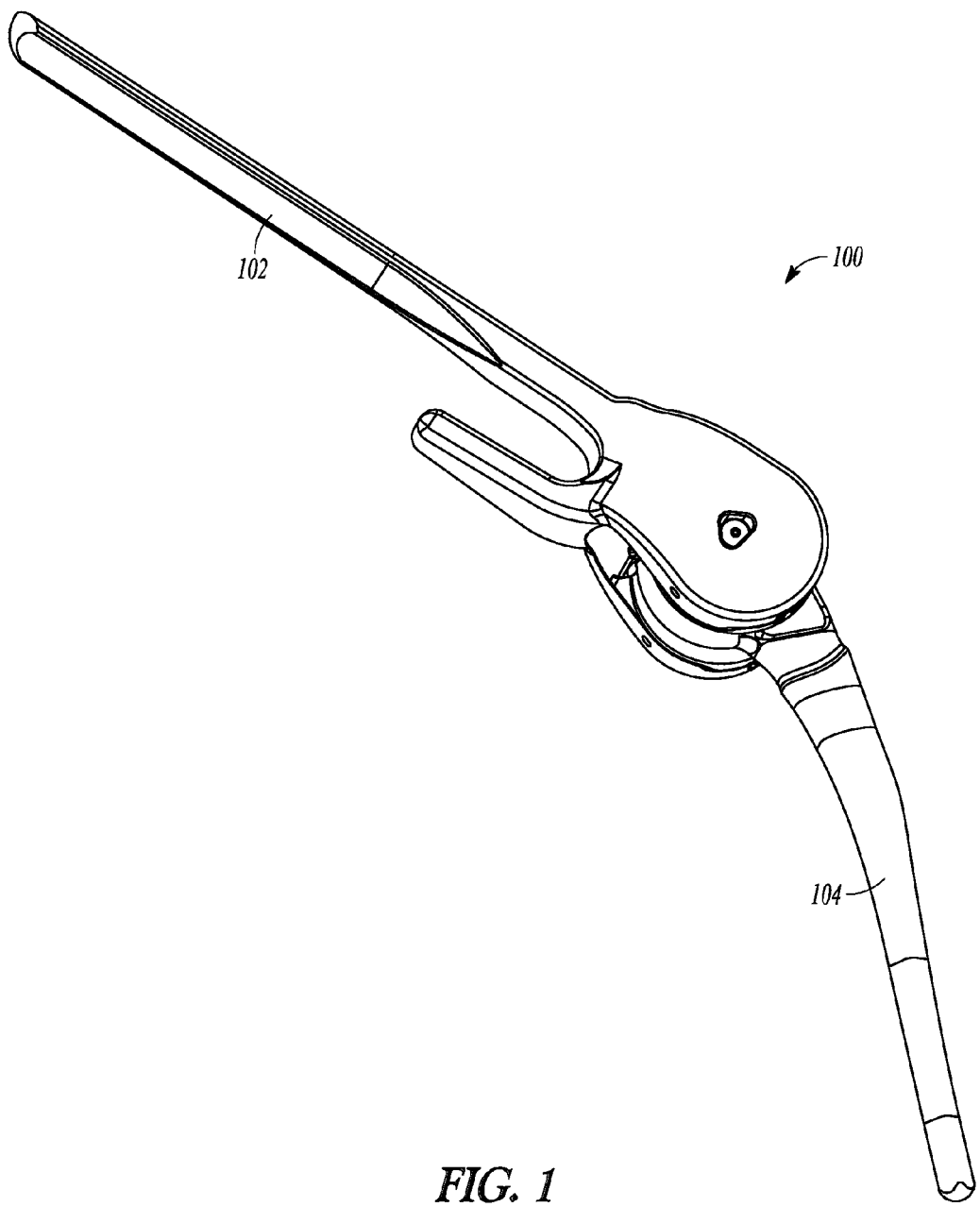
FIG. 1 is a perspective view of one example of an elbow prosthesis in accordance with the present patent application.

The present application relates to devices and methods for an elbow prosthesis that can be used in an elbow arthroplasty procedure. FIG. 1 shows an example of an elbow prosthesis 100 that can include a humeral component 102 and an ulnar component 104. The elbow prosthesis 100, as shown in FIG. 1, is oriented anatomically (i.e. how the elbow prosthesis 100 would be oriented if implanted in a body of a patient) and the ulnar component 104 is at an angle of approximately forty-five (45) degrees, relative to the humeral component 102. The humeral component 102 can be partially received within a humeral medullary canal, and the ulnar component 104 can be partially received within an ulnar medullary canal. As will be described in further detail below, the elbow prosthesis 100 can include a suitable connection means that can allow for pivoting movement of the ulnar component 104 relative to the humeral component 102.

Figure 2:
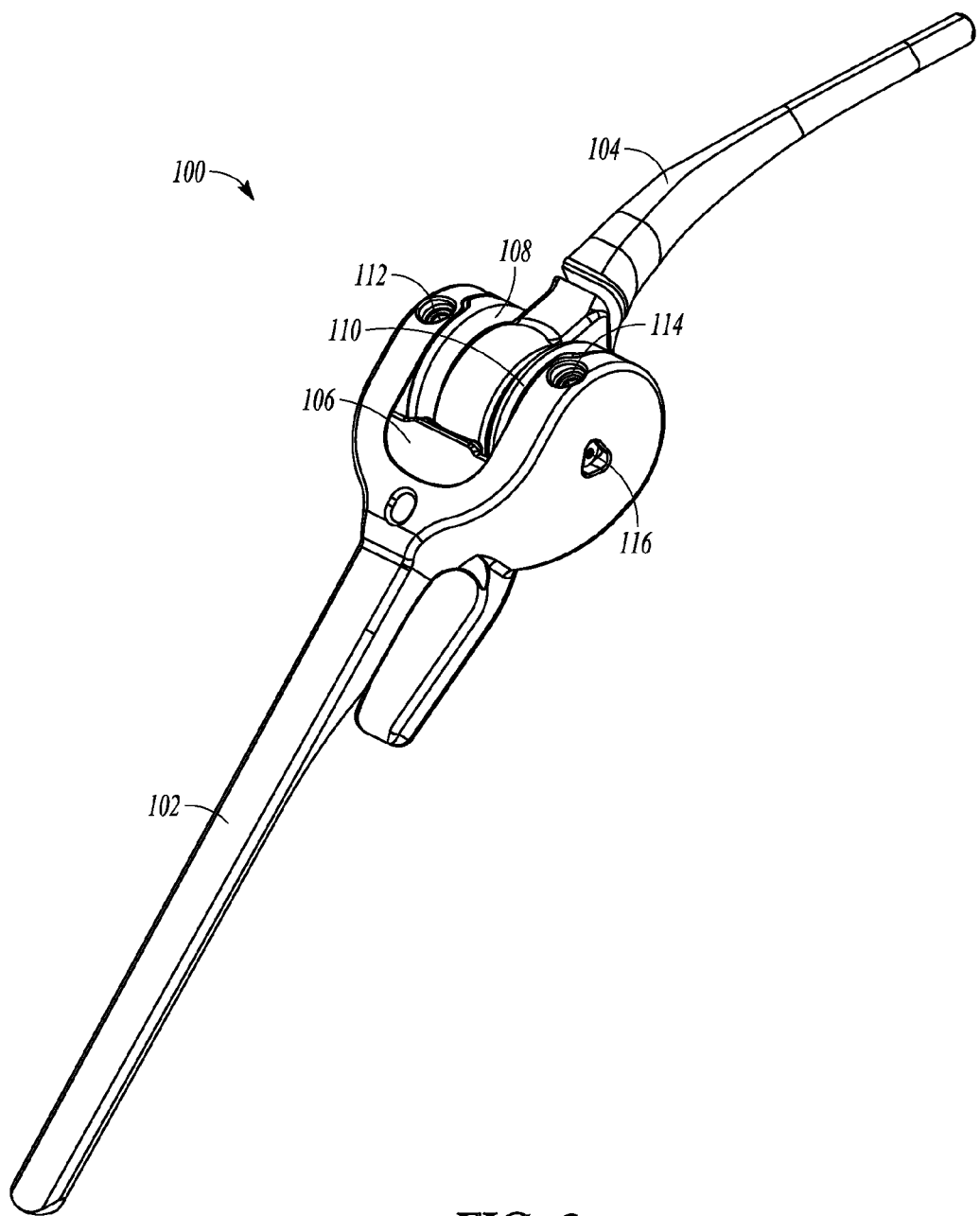
FIG. 2 is a perspective view of the elbow prosthesis of FIG. 1, rotated approximately 180 degrees.

FIG. 2 shows the elbow prosthesis 100 rotated approximately 180 degrees relative to what is shown in FIG. 1. The elbow prosthesis 100 can include the humeral component 102, the ulnar component 104, a humeral bearing 106, a first ulnar bearing 108, a second ulnar bearing 110, a first fastener 112, a second fastener 114, and a pin 116. Each of these components is also shown in FIG. 3, which is an exploded view of the elbow prosthesis 100 shown in FIG. 2.

Figure 3:
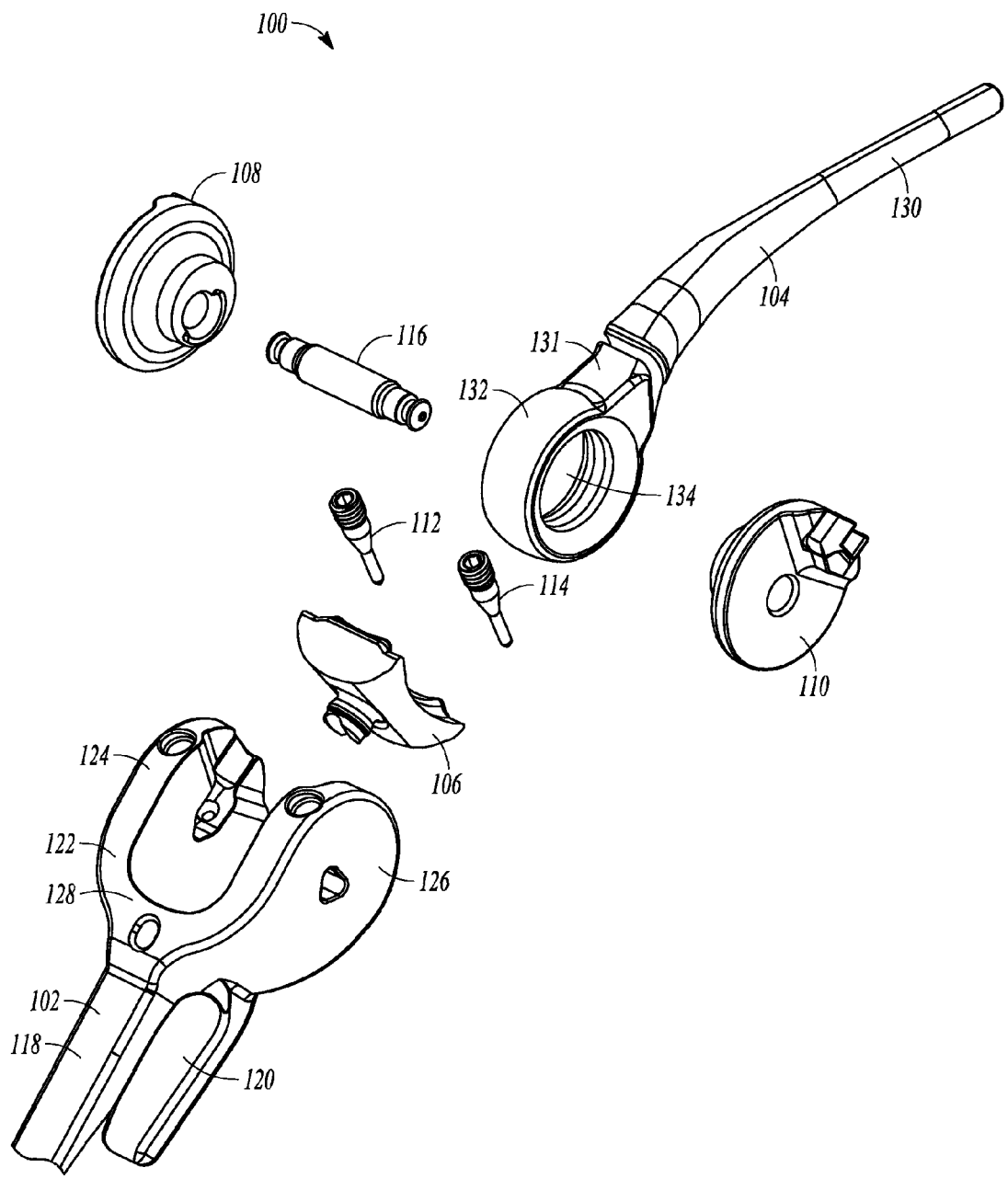
FIG. 3 is an exploded perspective view of the elbow prosthesis of FIG. 2.

With reference to FIG. 3, the humeral component 102 can include a humeral stem 118, a flange 120, and a yoke 122 extending from the humeral stem 118. The yoke 122 can include a first ear 124 and a second ear 126. The humeral bearing 106 can be positioned in or coupled to a base 128 of the yoke 122.

The ulnar component 104 can include an ulnar stem 130, an ulnar head 132 having an aperture or opening 134 extending through the ulnar head 132, and an ulnar neck 131 between the head 132 and the stem 130. The ulnar head 132 can also be referred to as an ulnar eye.

Each of the first 108 and second 110 ulnar bearings can extend into the aperture 134 of the ulnar head 132. The pin 116 can extend through the first ulnar bearing 108, the ulnar head 132, and the second ulnar bearing 110. Opposing end portions of the pin 116 can extend into the first 124 and second 126 ears of the yoke 122 of the humeral component 102. When assembled to the humeral component 102, the pin 116 can define an axis upon which the ulnar component 104 can pivot relative to the humeral component 102.

The first fastener 112 can extend into the first ear 124 of the yoke 122 and the second fastener 114 can extend into the second ear 126 of the yoke 122 to secure the humeral 102 and ulnar 104 components to one another. In an example, the first 112 and second 114 fasteners can be a first screw and a second screw, respectively. The engagement between the first fastener 112, the first ear 124, and the pin 116, as well as a similar engagement between the second fastener 114, the second ear 126, and the pin 116, is described in further detail below.

When the humeral component 102 and the ulnar component 104 are implanted into a humerus and an ulna, respectively, of a patient, the yoke 122 of the humeral component 102 and the ulnar head 132 of the ulnar component 104 can remain exposed. The ulnar head 132 can be configured to pivot about the pin 116 to enable movement of the ulnar component 104 relative to the humeral component 102, as described above.

The humeral component 102 and/or the ulnar component 104 can be made of one or more materials suitable for implantation within a human or animal body. These materials can include, but are not limited to, stainless steel, titanium, cobalt, or one or more alloys thereof. In an example, the humeral component 102 can be titanium. In an example, the ulnar component 104 can be titanium. The ulnar head 132 of the ulnar component 104 can include a surface treatment that can improve wear resistance of the ulnar head 132 as it articulates against a bearing surface. An example of such a surface treatment can include surface nitriding as disclosed in U.S. Publication No. 2010/0051141.

Figure 4C:
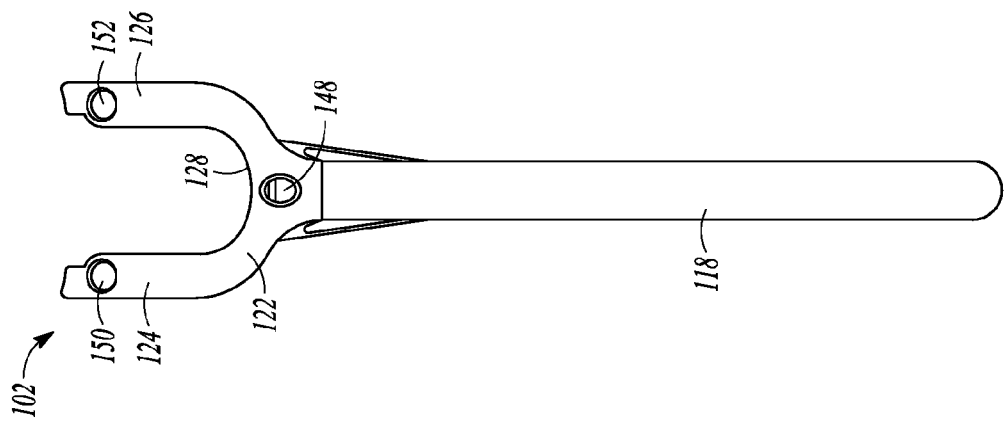
FIG. 4C is a back view of the humeral component of FIG. 4A.
Figure 4B:
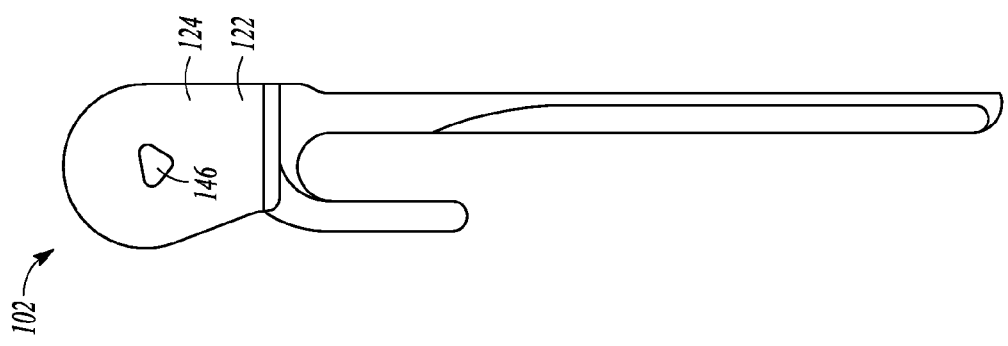
FIG. 4B is a side view of the humeral component of FIG. 4A.
Figure 4A:
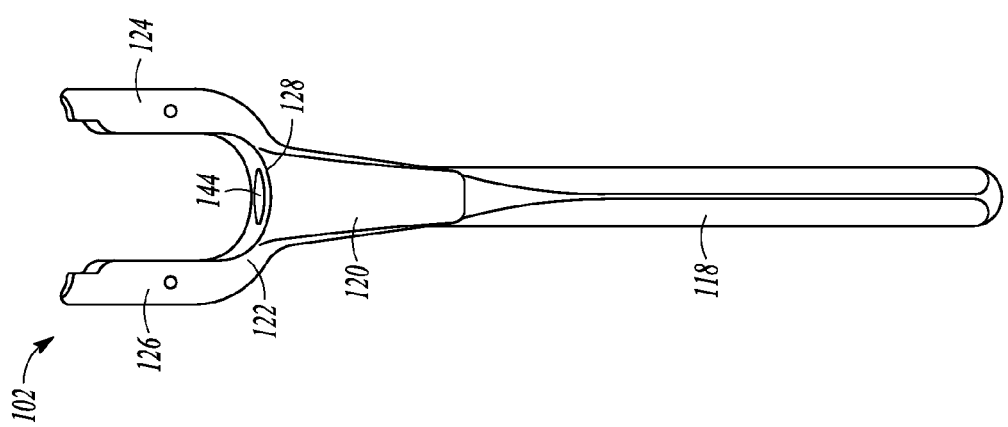
FIG. 4A is a front view of a humeral component of the elbow prosthesis in accordance with the present patent application.

FIGS. 4A-4E show various views of the humeral component 102. FIG. 4A is a view of an anterior side of the humeral component 102, and shows the humeral stem 118, the flange 120, and the yoke 122 including the first 124 and second 126 ears extending from the base 128 of the yoke 122. The base 128 can include a recess or opening 144 extending into the base 128.

FIG. 4B is a view of a lateral side of the humeral component 102. As shown in FIG. 4B, the first ear 124 of the yoke 122 can include an opening 146. In an example, the opening 146 can be a generally V-shaped opening. In some examples, the V-shaped opening 146 can be configured for a specific engagement with the pin 116, as described further below. In other examples, any suitable shape for the opening 146 can be utilized. The second ear 126 can include a similar opening, which is described in further detail below.

FIG. 4C is a view of a posterior side of the humeral component 102. The humeral component 102 can include a hole or opening 148 in the base 128 of the yoke 122, on the posterior side and near the stem 118. The opening 148 can be used as an access hole for a surgical tool configured to assist with implantation of the elbow prosthesis 100 during surgery and/or during a post-implant surgery. The humeral component 102 can include a first bore 150 in the first ear 124 and a second bore 152 in the second ear 126. In an example, the first 150 and second 152 bores can be threaded bores.

Figure 4D:
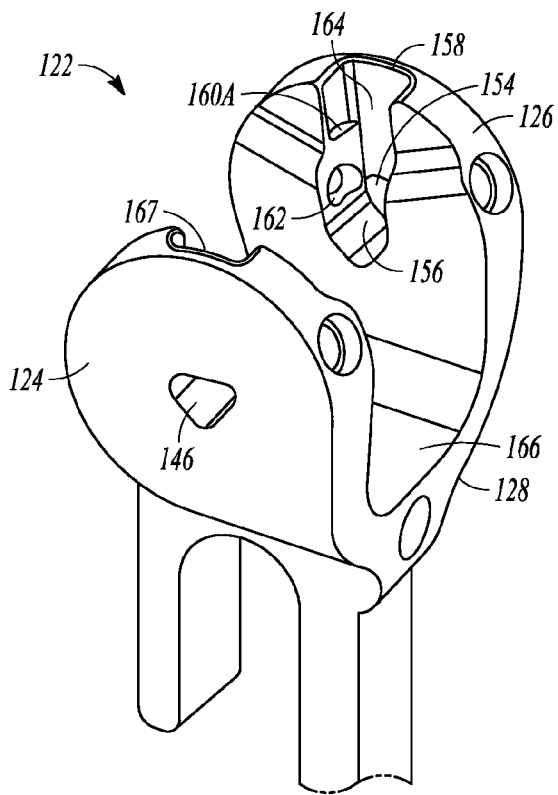
FIGS. 4D and 4E are perspective views of a yoke of the humeral component of FIG. 4A.
Figure 4E:
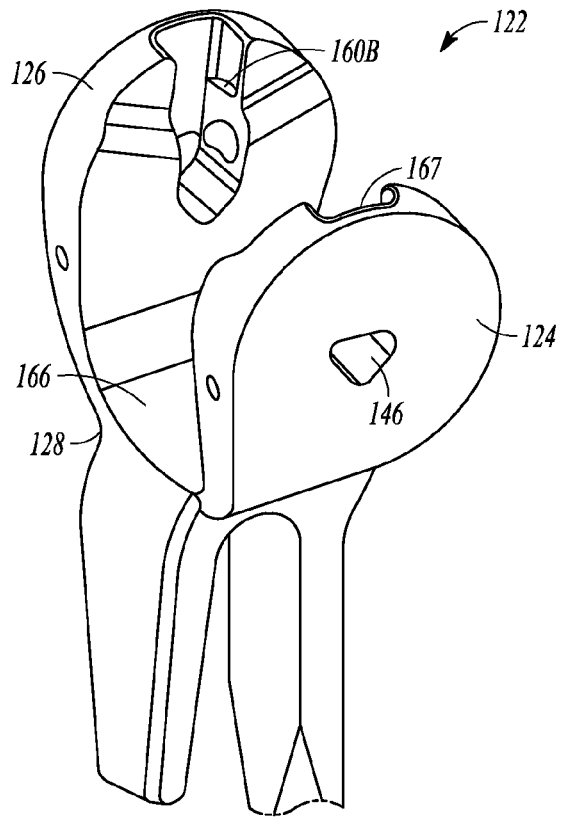

FIGS. 4D and 4E are perspective views of a portion of the humeral component 102 illustrating various features of the yoke 122, including features of the first 124 and second 126 ears. FIGS. 4D and 4E generally show an exterior of the first ear 124 and an interior of the second ear 126. In an example, the first 124 and second 126 ears are substantially similar.

The second ear 126 can include an opening 154, similar to the opening 146 on the first ear 124. In an example, the opening 154 can be a generally V-shaped opening. The opening 154 can extend through the second ear 126 to form a generally V-shaped seat 156 in the second ear 126. The opening 154 can be sized, shaped, or otherwise configured to receive the pin 116.

As shown in FIGS. 4D and 4E, the openings 146 and 154 can extend from an inside surface to an outside surface of the ears 124 and 126, respectively. In other examples, the openings 146 and 154 do not extend through to the outside surfaces of the ears 124 and 126, depending, for example, on how the openings 146 and 154 are formed during the manufacture of the humeral component 102. The openings 146 and 154 can be formed in order to form the V-shaped seats (seat 156) inside the first 124 and second 126 ears. An engagement of the pin 116 in the v-shaped seat 156 is described further below.

The second ear 126 can include a recess 158 formed in an upper portion of the second ear 126. The recess 158 can include at least one surface contour feature 160A formed on an interior wall of the second ear 126. The feature 160A, shown in FIG. 4D, can be sized, shaped, or otherwise configured to increase a distance between two inside walls forming the recess 158, such that a width between the inside walls can be more than a width of an opening defining the recess 158. This difference in width between the inside walls and the opening of the recess 158 can provide a press-fit when a tab on one of the ulnar bearings (see FIGS. 8A and 8B) is inserted into the recess 158. A surface contour feature 160B is shown in FIG. 4E on an opposite wall from the feature 160A.

The second ear 126 can include a second recess 164 formed between the opening 154 and the recess 158; the second recess 164 can be sized, shaped, or otherwise configured to allow passage of one of the screws (see FIG. 5), as described further below. The second ear 126 can include a first channel 162 formed through an interior of the second ear 126. The first channel 162 can be sized, shaped, or otherwise configured to receive an end portion of one of the fasteners and can be aligned with at least a portion of the second recess 164. In an example, the recess areas 158 and 164, and the opening 154 can form one generally continuous recess in the second ear 126.

The yoke 122 can include a seating surface 166 in the base 128 of the yoke 122. The seating surface 166 can include the recess 144 (see FIG. 4A).

A recess 167 can be formed in an upper portion of the first ear 124, similar to the recess 158 of the second ear 126. The other corresponding features on the interior of the first ear 124 are generally not visible in FIGS. 4D and 4E; in an example, these corresponding features of the first ear 124 can be substantially similar to those of the second ear 126.

Figure 5:
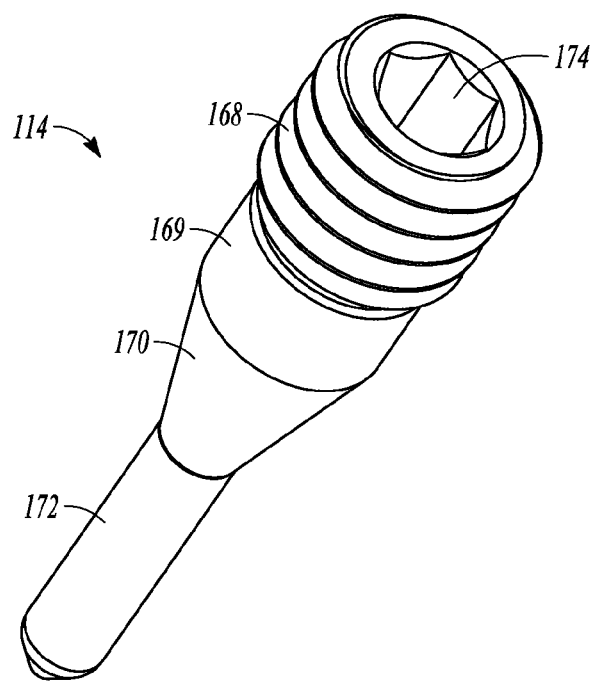
FIG. 5 is a perspective view of a fastener of the elbow prosthesis in accordance with the present patent application.

FIG. 5 is a perspective view of the second screw 114. In an example, the first screw 112 can be substantially similar to the second screw 114. The second screw 114 can include a threaded portion 168, a cylindrical (tapered) portion 169, a conical portion 170, and an end portion 172. In an example, as shown in FIG. 5, the threaded portion 168 can be externally threaded. In certain examples, the threaded portion 168 can be internally threaded. The threaded portion 168 can have a larger diameter than the end portion 172. The cylindrical portion 169 and the conical portion 170 can be a non-threaded portion of the screw 114. The screw 114 can include an internal drive feature 174 that allows for use of a tool to fasten the screw 114 to another component, such as the second ear 126 of the yoke 122. In certain examples, the screw 114 can include an external drive feature.

The first 112 and second 114 screws can be made of one or more materials suitable for implantation within a human or animal body. These materials can include, but are not limited to, stainless steel, titanium, cobalt, or one or more alloys thereof. In an example, the first 112 and second 114 screws can be cobalt chrome.

Figure 6:
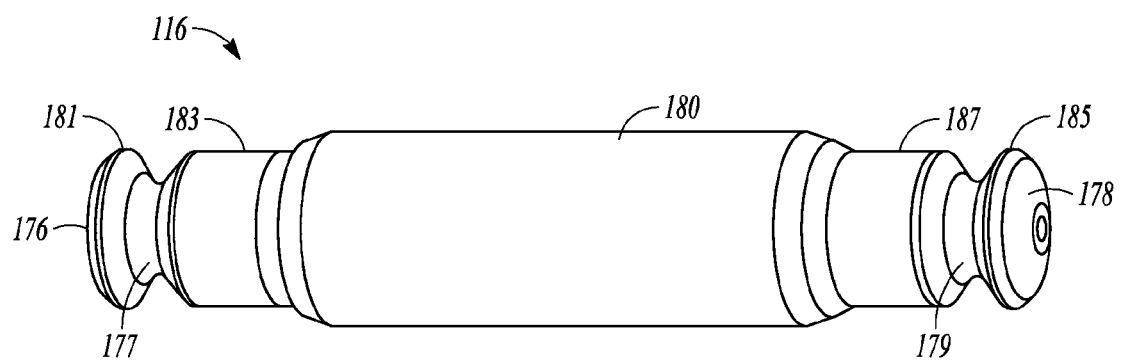
FIG. 6 is a perspective view of a pin of the elbow prosthesis in accordance with the present patent application.

FIG. 6 is a perspective view of the pin 116, which can include a first end portion 176, a second end portion 178, and a main body portion 180. The first end portion 176 can include a first groove 177, a first outer diameter 181, and a first inner diameter 183. The second end portion 178 can include a second groove 179, a second outer diameter 185, and a second inner diameter 187. As shown in FIG. 6, the main body portion 180 can have a larger diameter than the inner diameters 183 and 187 and the outer diameters 181 and 185 of the first 176 and second 178 end portions.

The pin 116 can be made of one or more materials suitable for implantation within a human or animal body and for enabling pivoting movement of one component relative to another component. These materials can include, but are not limited to, stainless steel, titanium, cobalt, or one or more alloys thereof. In an example, the pin 116 can be cobalt chrome.

Figure 7:
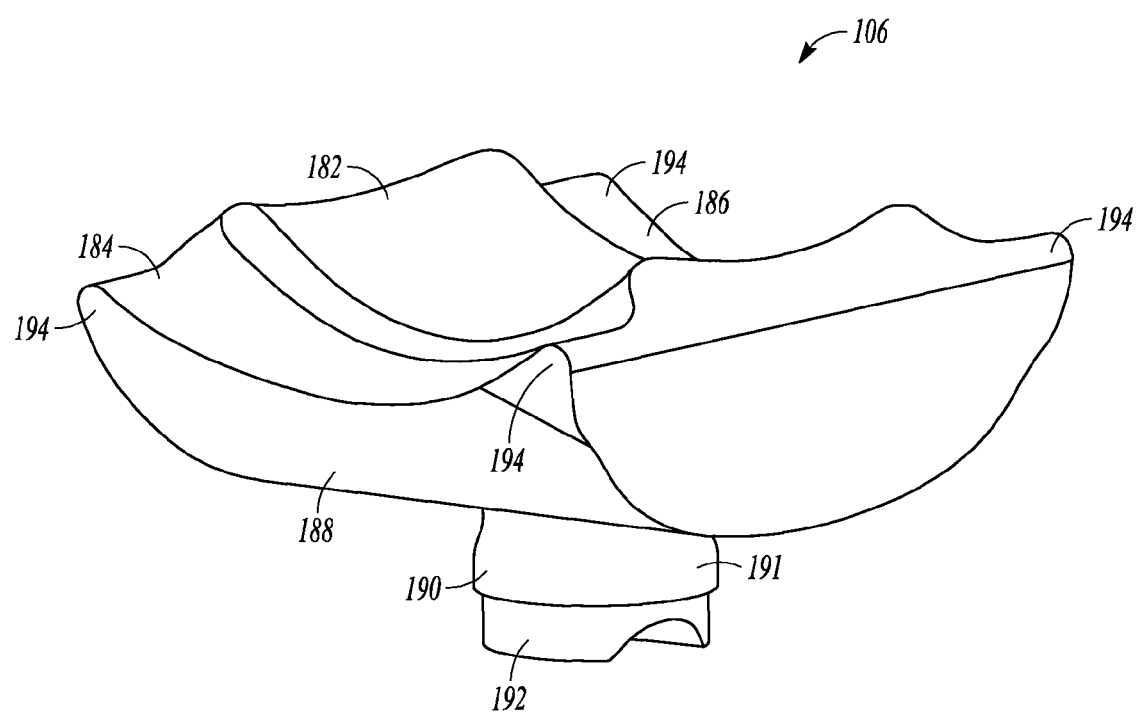
FIG. 7 is a perspective view of a humeral bearing of the elbow prosthesis in accordance with the present patent application.

FIG. 7 is a perspective view of the humeral bearing 106, which can include an articulation surface 182, a first rail 184, a second rail 186, a seating surface 188, and a peg 190. The humeral bearing 106 can be attached to the base 128 of the yoke 122 of the humeral component 102, such as by inserting the peg 190 into the recess 144 in the yoke 122 (see FIG. 4A). The connection between the humeral bearing 106 and the humeral component 102 is described further below in references to FIGS. 11 and 12. The peg 190 can include a collar portion 191 and a base portion 192.

The articulation surface 182 of the humeral bearing 106 can be sized, shaped, or otherwise configured such that the ulnar head 132 of the ulnar component 104 can articulate against the articulation surface 182 when the ulnar component 104 pivots relative to the humeral component 102.

The humeral bearing 106 can include four ears 194; two ears 194 can be located at the corners formed between the seating surface 188 and the first rail 184, and two ears 194 can be formed at the corners formed between the seating surface 188 and the second rail 186. The ears 194 can facilitate a secure fit of the humeral bearing 106 in the base 128 of the yoke 122, such as through a press fit of the ears 194 into the base 128 of the yoke 122, and can limit movement of the humeral bearing 106, for example, when forces are applied to the humeral bearing 106.

Figure 8A:
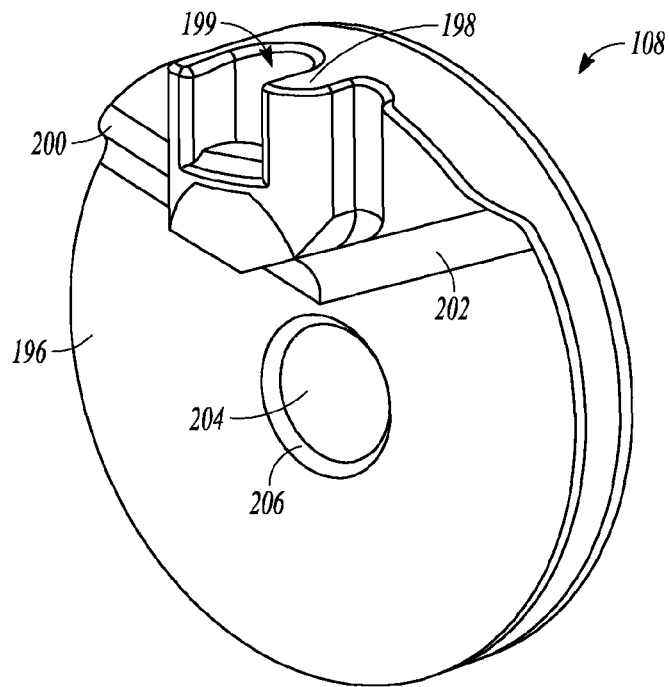
FIGS. 8A and 8B are perspective views of an ulnar bearing of the elbow prosthesis in accordance with the present patent application.
Figure 8B:
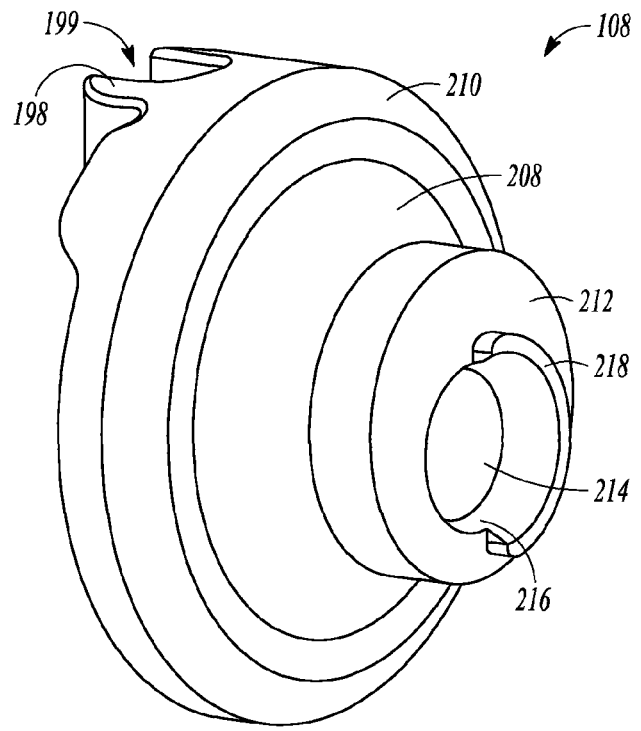

FIGS. 8A and 8B show two perspective views of the first ulnar bearing 108. FIG. 8B shows the first ulnar bearing 108 rotated approximately 90 degrees relative to the view shown in FIG. 8A. The first ulnar bearing 108 can include an external face 196, a tab 198, a slot 199, and shoulders 200 and 202 on each side of the tab 198. The external face 196 can be a seating surface between the first ulnar bearing 108 and the first ear 124 of the yoke 122.

The first ulnar bearing 108 can include a first opening or hole 204 for receiving the pin 116. In an example, the first hole 204 can include a chamfer 206 to help lead the pin 116 through the first hole 204.

The first ulnar bearing 108 can include a first bearing extension 208 having an articulation surface 210 and an end face 212. A second opening or hole 214 can extend through the end face 212 for receiving the pin 116. In an example, the second hole 214 can include a chamfer 216 to help lead the pin 116 through the second hole 216. A compression rib 218 can extend from the end face 212 on at least a portion of the end face 212. The first 204 and second 214 holes can converge within the first ulnar bearing 108 so as to form a single continuous channel that is structured to allow passage of the pin 116.

In an example, the second ulnar bearing 110 can be substantially similar to the first ulnar bearing 108. When rotated by approximately 180 degrees relative to the position in FIG. 8A, the second ulnar bearing 110 can mate with the first ulnar bearing 108.

The humeral bearing 106 and/or the first 108 and second 110 ulnar bearings can be made of one or more materials suitable for implantation within a human or animal body. In an example, the humeral bearing 106 and/or the first 108 and second ulnar bearings 110 can be made of an elastomeric material, such as, for example, a ultrahigh molecular weight polyethylene (UHMWPE). In an example, the humeral bearing 106 can be formed from a crosslinked ultrahigh molecular weight polyethylene blend stabilized with Vitamin E, such as disclosed in U.S. Pat. No. 7,846,376. In an example, the first 108 and second 110 ulnar bearings can be formed from a crosslinked ultrahigh molecular weight polyethylene blend stabilized with Vitamin E. When formed from an elastomeric material, the bearings 106, 108 and 110 can be squeezed or compressed, for example to overcome an interference fit or press fit, and/or conform to a surrounding metal component.

Figure 9:
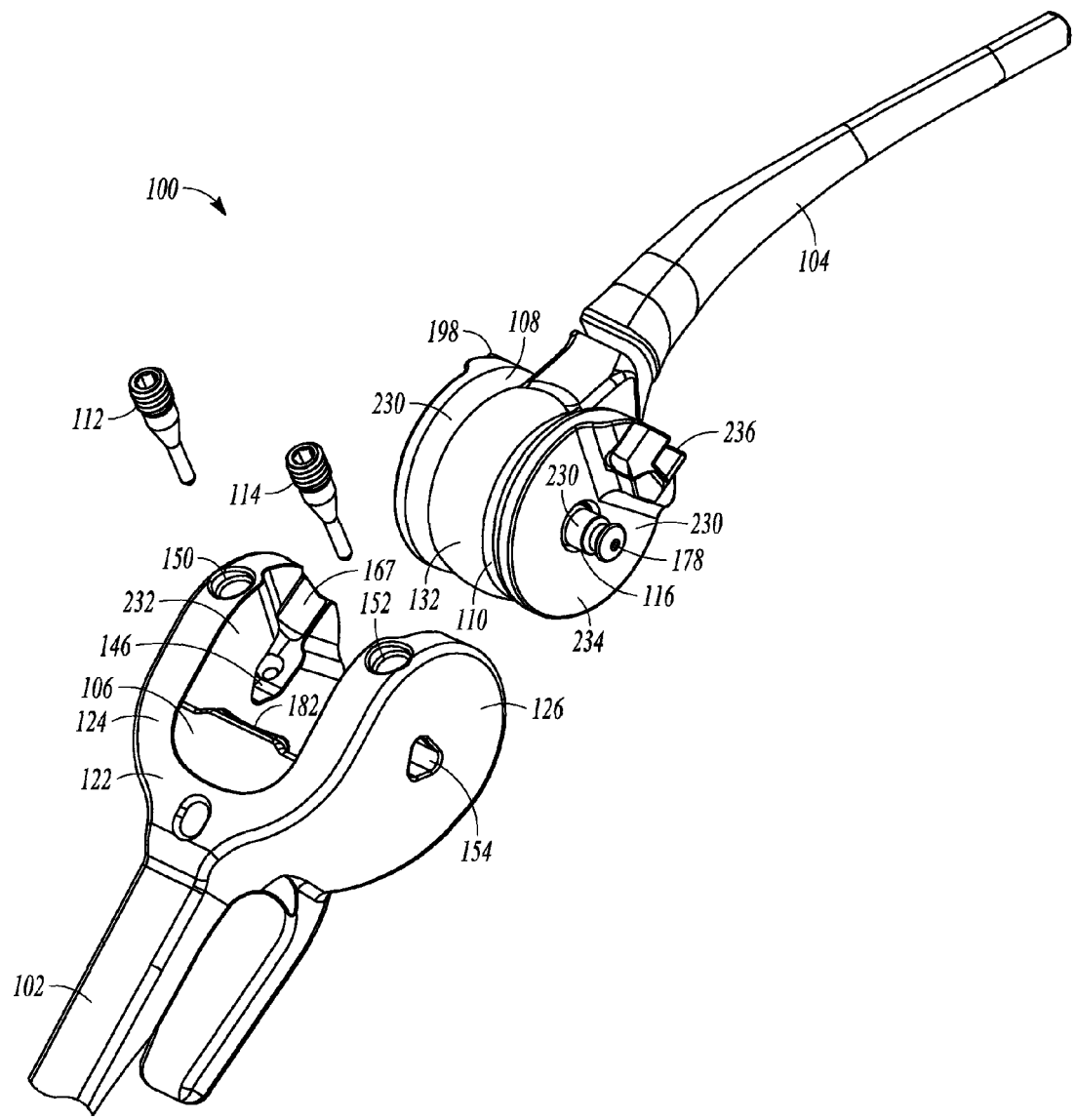
FIG. 9 is a perspective view of the elbow prosthesis of FIGS. 1-3 in a partially assembled state.

FIG. 9 shows the elbow prosthesis 100 of FIGS. 1-3 in a partially assembled position. As shown in FIG. 9, a bearing assembly 230 can be assembled onto the ulnar head 132 of the ulnar component 104. The bearing assembly 230 can include the first ulnar bearing 108, the second ulnar bearing 110, and the pin 116. The first bearing extension 208 of the first ulnar bearing 108 (see FIG. 8B) can extend into the aperture 134 of the ulnar head 132. A second bearing extension on the second ulnar bearing 110 can extend into the aperture 134 such that when the bearing assembly 230 is assembled onto the ulnar head 132, the end face 212 of the first ulnar bearing 108 (see FIG. 8B) can contact an end face on the second ulnar bearing 110. The main body portion 180 of the pin 116 (see FIG. 6) can extend through the first ulnar bearing 108, the ulnar head 132, and the second ulnar bearing 110; the first end portion 176 (see FIG. 6) and the second end portion 178 of the pin 116 can remain exposed at this point in the assembly of the elbow prosthesis 100. When the first 108 and second 110 ulnar bearings are assembled onto the pin 116, the end faces can contact one another; in an example, a compression of the first 108 and second 110 ulnar bearings with one another can occur at a later step when the bearings 108 and 110 and the ulnar component 104 can be attached to the humeral component 102.

A next step in the assembly of the elbow prosthesis 100 can include connecting the ulnar component 104 to the humeral component 102, which can include placing the first end portion 176 of the pin 116 into the first ear 124 of the yoke 122 and placing the second end portion 178 of the pin 116 into the second ear 126 of the yoke 122. The pin 116 and the first 124 and second 126 ears of the yoke 122 are each configured such that the first end portion 176 of the pin 116 can be secured inside the opening 146 formed in the first ear 124 and the second end portion 178 of the pin 116 can be secured inside the opening 154 formed in the second ear 126.

As described above, the first 108 and second 110 ulnar bearings can be formed of one or more elastomeric or compressible materials such the first 108 and second 110 ulnar bearings can be squeezed or compressed together as the bearing assembly 230 and the ulnar component 104 are assembled onto the humeral component 102. In an example, when the first 108 and second 110 ulnar bearings are squeezed together, the compression rib 218 on the first ulnar bearing 108 (see FIG. 8B) can compress against an end face on the second ulnar bearing 110, and a compression rib on the second ulnar bearing 110 can compress against the end face 212 on the first ulnar bearing 108 (see FIG. 8B). In an example, the compression ribs can each be generally semi-circular such that the when the end faces of the first 108 and second 110 ulnar bearings are in contact, the compression ribs together form a generally circular shape.

Once the ulnar bearing assembly 230 is attached to the humeral component 102, the first 108 and second 110 ulnar bearings can be secured within the yoke 122. In an example, the external face 196 of the first ulnar bearing 108 (see FIG. 8A) can contact an inner surface 232 of the first ear 124, and an external face 234 on the second ulnar bearing 110 can contact an inner surface of the second ear 126. The tab 198 on the first ulnar bearing (see FIG. 8A) can be press fit into the recess 167 formed in the upper portion of the first ear 124; a tab 236 on the second ulnar bearing 110 can be press fit into the recess 158 formed in the upper portion of the second ear 126 (see FIG. 4D). In an example, the tab 198 on the first ulnar bearing 108 can be compressed during insertion of the tab 198 into the recess 167, until the tab 198 is through an opening of the recess 167, at which point the tab 198 can relax and conform to a space within the recess 167. As discussed above, surface contour features 160A and 160B formed on the inside walls of the recesses in the first 124 and second 126 ears can facilitate the press-fit.

A next step in the assembly of the elbow prosthesis 100 can include inserting the first fastener 112 through the bore 150 of the first ear 124 and inserting the second fastener 114 through the bore 152 of the second ear 126. This is further described below in reference to FIG. 10. Once the assembly is complete, the ulnar component 104 can pivot about the pin 116 such as to provide pivotal movement of the ulnar component 104 relative to the humeral component 102. As the ulnar component 104 moves, the ulnar head 132 can articulate against the articulation surface 182 of the humeral bearing 106.

The assembly of the elbow prosthesis 100 can be configured such that the bearings 106, 108 and 110, or at least one feature on the bearings 106, 108 and 110, can compress during an assembly of the elbow prosthesis 100 and then relax and conform to a surrounding area. Various features on the bearings, such as the tabs described above, or the ears 194 on the humeral bearing 106, can allow an interference fit or press fit that can result in a stable placement of the bearings in the elbow prosthesis 100, such as to reduce or eliminate any movement of the bearings 106, 108, and 110 within the elbow prosthesis 100, particularly as various forces or loads are placed on the bearings 106, 108, and 110. In certain examples, alternative or additional features to those described herein can be used on the bearings 106, 108, 110 to provide a press fit.

Figure 10A:
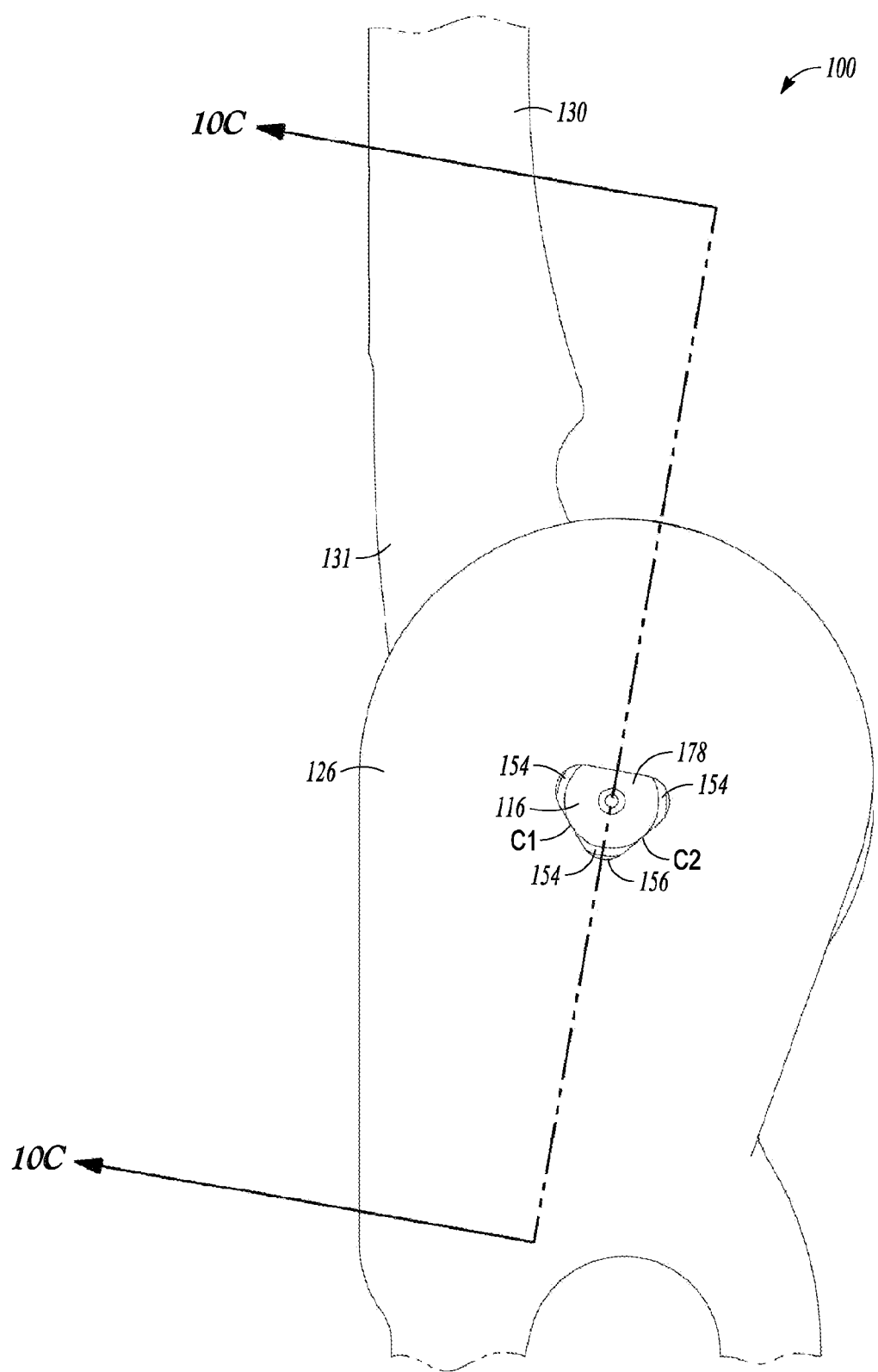
FIG. 10A is a side view of a portion of the elbow prosthesis of FIG. 9 in an assembled state.

FIG. 10A is a side view of a portion of the elbow prosthesis 100 as assembled, showing the second ear 126 of the humeral component 102 and a portion of the ulnar component 104, including the ulnar neck 131 and a portion of the stem 130. As shown in FIG. 10A, the second end portion 178 of the pin 116 can be seated inside the opening 154 formed in the second ear 126. In an example, the opening 154 can be generally V-shaped and the end portion 178 of the pin 116 can have at least two points of contact C1 and C2 with a seat 156 formed by the opening 154. The seat 156 can be sized, shaped, or configured to keep the pin 116 in a desired position and limit or resist movement of the pin 116. The first end portion 176 of the pin 116 can be similarly seated inside the opening 146 formed in the first ear 124. The position of the pin 116 in the opening 154 is described further below in reference to FIGS. 10C and 10D. The same description generally applies to the position of the pin 116 in the opening 146. As described above in reference to FIGS. 4D and 4E, the openings 146 and 154 may not, in some examples, extend through to an outside of the ears 124 and 126. The openings 146 and 154 can be configured to create the v-shaped seats inside the ears 124 and 126 for engaging with the pin 116.

Figure 10B:
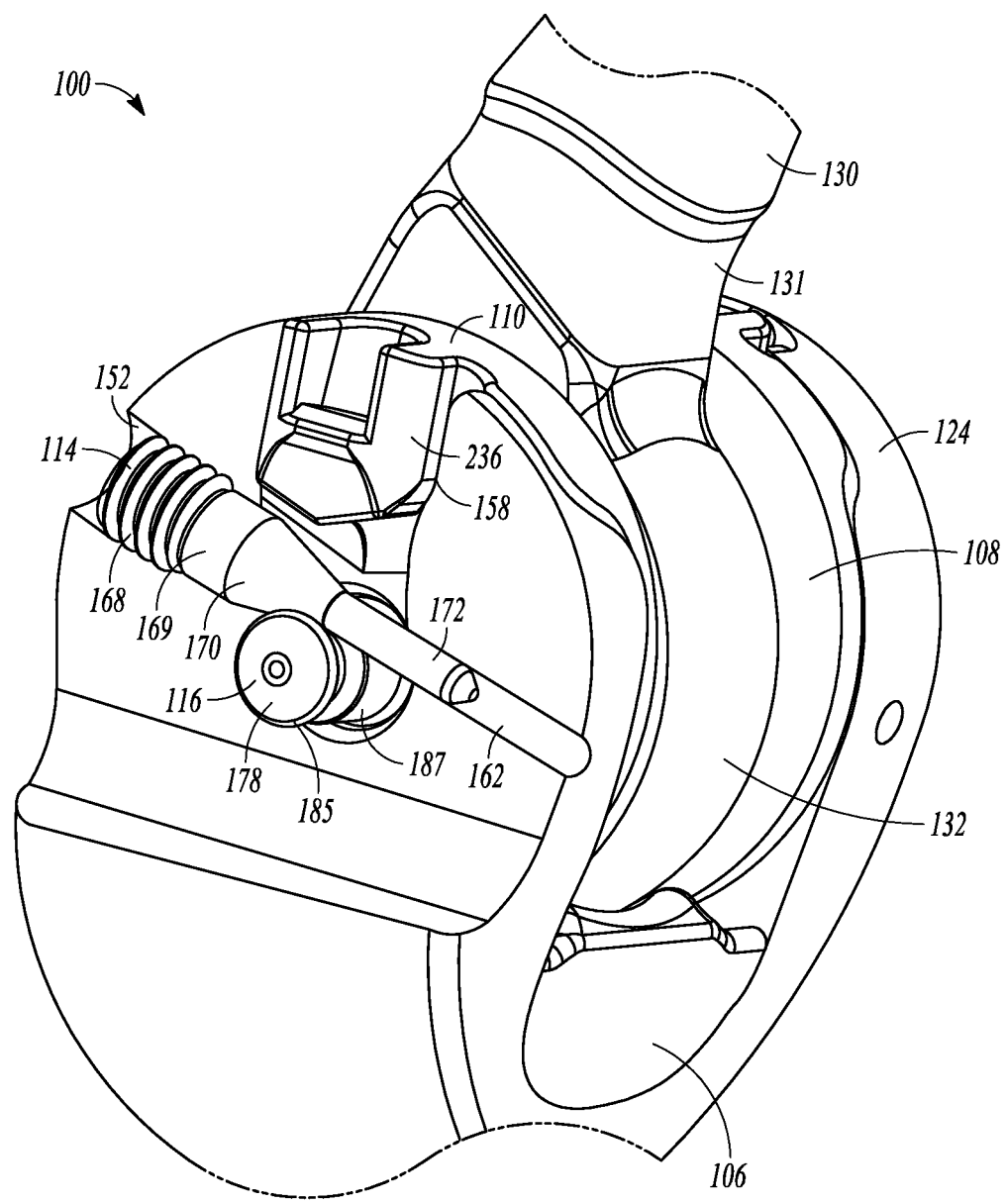
FIG. 10B is a perspective view of a portion of the elbow prosthesis of FIG. 10A with a portion of the yoke of the humeral component partially cut-away.

FIG. 10B is a perspective view of the assembled elbow prosthesis 100 of FIG. 10A with a portion of the second ear 126 of the humeral component 102 cut-away in order to show the various components inside and surrounding the second ear 126. In addition to the second ear 126, FIG. 10B shows the second end portion 178 of the pin 116, the screw 114, the second ulnar bearing 110, the ulnar head 132, the first ulnar bearing 108, and the first ear 124. The second screw 114 can extend into the second ear 126. In an example, the second screw 114 can extend into the second ear 126 at an angle in the anterior-posterior direction. The threaded portion 168 of the screw 114 can engage with a threaded bore 152 in the second ear 126. The conical or non-threaded portion 170 can engage with the second end 178 of the pin 116. The conical portion 170 can engage with the groove 179 (FIG. 6) of the pin 116 between the inner 187 and outer 185 diameters of the end portion 178. The end portion 172 of the screw 114 can be received in the channel 162 formed in the second ear 126.

As shown in FIG. 10B and described above in reference to the tab 198, the tab 236 on the second ulnar bearing 110 can be press fit into the recess 158 of the second ear 126 to secure the second ulnar bearing 110 to the second ear 126 and minimize or resist movement of the second ulnar bearing 110.

Figure 10C:
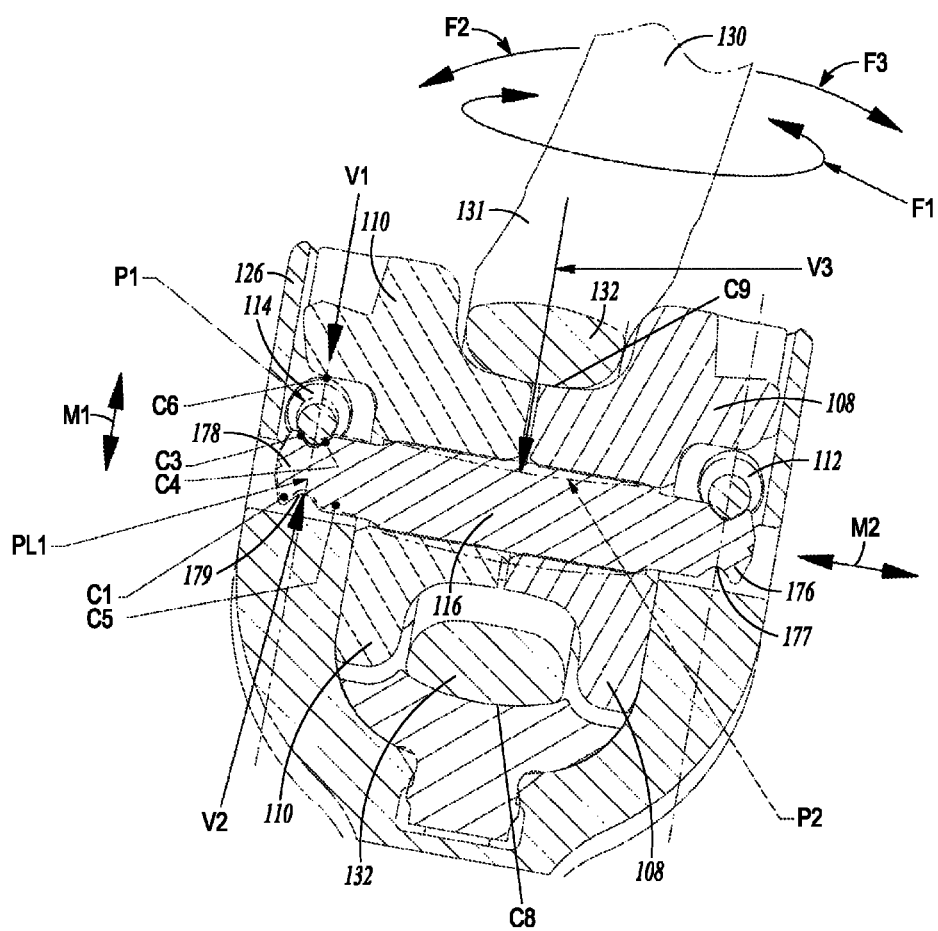
FIG. 10C is a cross sectional view of a portion of the elbow prosthesis of FIG. 10A.

FIG. 10C is a cross-sectional view of the elbow prosthesis 100 taken along the line 10C-10C in FIG. 10A. FIG. 10C shows an engagement between the second end portion 178 of the pin 116 and the conical portion 170 of the second screw 114, as well as an engagement between the first end portion 176 of the pin 116 and the first screw 112. The engagement between the second screw 114 and the pin 116 is described in further detail herein in reference to FIGS. 10C and 10D; the engagement between the first screw 112 and the pin 116 can be substantially similar. Contact areas C8 and C9 shown in FIG. 10C are described below in reference to FIG. 13B.

When the elbow prosthesis 100 is implanted in an elbow of a patient, the prosthesis can undergo various anatomic forces or loads, including an internal/external rotation force F1, a varus load F2, and a valgus load F3. A compressive joint load, which can occur in a general direction represented as a vector V3 in FIG. 10C, can be one of the highest forces on the prosthesis 100 and can also be referred to as an anatomic load. The design of the screw 114 and the pin 116, and their placement in the humeral component 102 can be configured to avoid or minimize exposure to cyclic transverse loading/unloading and/or load reversal, and to minimize or resist unloading of any of the components, in particular the screw 114, even under the various forces and high compressive joint loading described above. As further described below, the screw 114 and the pin 116 can be configured to minimize or resist loosening of the screw 114 over time, as compared to other prosthesis designs in which the screw can become looser. A specific engagement of the screw 114 with the pin 116 can be used to hold the pin 116 in place even under high compressive joint loads. As described further below, the screw 114 and the pin 116 can resist micro-motion in at least one direction.

The conical portion 170 of the screw 114 (FIG. 10B) can be received in the groove 179 formed in the second end portion 178 of the pin 116. In an example, the conical portion 170 of the screw 114 can have at least two points of contact C3 and C4 with the pin 116, such points of contact can generally be centered around the groove 179 in the pin 116. (A plane in the center of the groove 179 is shown as PL1 in FIG. 10C.) The screw 114 can serve as a wedge to hold the pin 116 within the second ear 126 and minimize or resist movement of the pin 116 as the pin 116 is exposed to various forces and loads. The points of contact C3 and C4 between the pin 116 and the screw 114 can help hold down the pin 116 to minimize movement of the pin 116 from side to side, especially when the prosthesis is exposed to the various forces described above and shown in FIG. 10C, and can help minimize or resist micro-motion in a direction indicated by M2 in FIG. 10C.

As described above in reference to FIG. 10A, the end portion of the pin 178 can have at least two points of contact C1 and C2 with the seat 156. In an example, the end portion 178 of the pin 116 can have four points of contact with the seat 156. The contact point C1 can be on the outer diameter 185 (FIG. 6) of the end portion 178 and another contact point C5 can be on the inner diameter 187 (FIG. 6) of the end portion 178. The contact point C2 can be similarly situated to the contact point C1, and although not visible in FIG. 10A or 10C, another contact point similarly situated to the contact point C5 can be on the inner diameter 187 of the end portion 178, adjacent to the contact point C2. These contact points of the pin 116 in the seat 156, in addition to the engagement of the screw 114 and the pin 116, can minimize or resist micro-motion in a direction indicated by M1 in FIG. 10C.

As the screw 114 is inserted into the bore 152 (FIG. 10B), the screw 114 can drive into the groove 179 in the pin 116 which can move the second end portion 178 of the pin 116 into the seat 156 of the ear 126 of the humeral component 102 (FIG. 10A). However, the pin 116 can move up and down or flex in response to forces on it, including the high compressive joint load, shown as the vector V3 in FIG. 10C. A profile P2 in FIG. 10C represents a profile of the pin 116 when under high compressive joint load. The pin 116 can thus flex back and forth, and as a result of the flexing action, the second end 178 of the pin 116 can move and push up on the screw 114 in a reactive load direction, represented by a vector V2 in FIG. 10C. (A profile of the screw 114 when under a maximum reactive load can be represented as a profile P1 in FIG. 10C.) The screw 114 can be tightened until the prescribed screw torque is reached, which can ensure that all the mating surfaces of the components are compressed together. As described above, the screw 114 can have various points of contact with the pin 116—thus the screw 114 can be supported by the pin 116 while the prescribed screw torque is being reached, which can allow the screw 114 to elastically bend away from the pin 116 as the screw 114 is driven in.

Elastic bending of the screw 114 can generate a force in a direction represented by a vector V1 in FIG. 10C—the force is a clamping load created by tightening of the screw 114. The clamping load can counteract the reactive load created by the pin 116 (reactive load direction represented as the vector V2). The clamping load by the screw 114 can secure the pin 116 against the seat 156.

As the screw 114 tightens and bends, the screw 114 can exert force on the pin 116. Over an operational life of the prosthesis 100, there can be wear that can cause the screw 114 to gradually rebound towards an unbent shape; however, even then, the screw 114 can continue to apply a compressive load on the pin 116 to resist micro-motion. Although the clamping load can decrease over time, a residual clamping load over the life of the prosthesis 100 can be maintained at the various contact points between the pin 116 and the screw 114, and the pin 116 and the seat 156. This residual clamp load can provide long-term resistance for loosening of the screw 114 and/or the resistance for the micro-motions mentioned above.

Figure 10D:
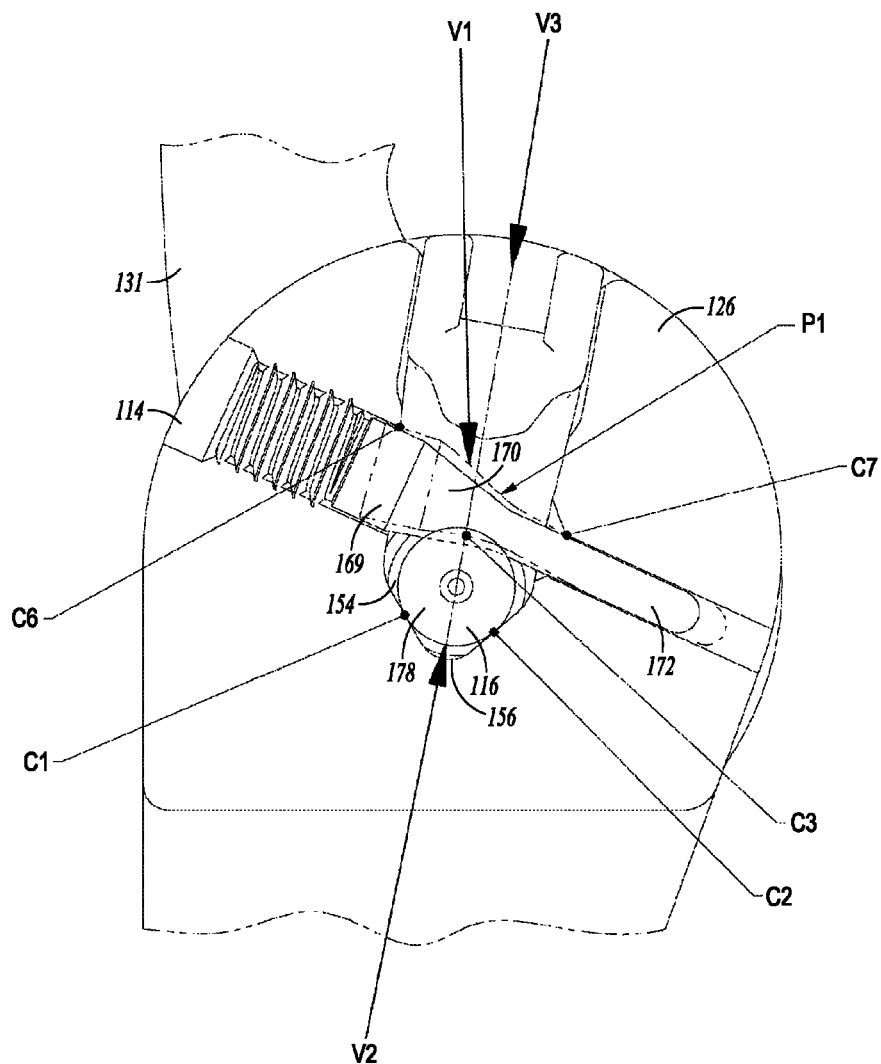
FIG. 10D is an end view of the portion of the elbow prosthesis of FIG. 10B.

As also shown in FIG. 10D, FIG. 10C shows the cylindrical portion 169 of the screw 114 having a point of contact C6 with an inside portion of the ear 126 of the humeral component 102.

FIG. 10D is an end view of the portion of the elbow prosthesis 100 shown in FIG. 10B. The profile P1 of the screw 114 under maximum reactive load can be seen in FIG. 10D. Moreover, FIG. 10D shows many of the contact points shown in FIG. 10C and described above. In addition to the contact point C6, the screw 114 can have at least one other point of contact C7 with the inside portion of the ear 126 of the humeral component 102. As shown in FIG. 10D, in an example, the end portion 172 of the screw 114 can have a point of contact C7 with the humeral component 102. In addition, the pin 116 has the four points of contact with the opening 154 in the ear 126, as described in reference to FIG. 10C. As stated above, these points of contact can help to minimize unloading and/or minimize or resist micro-motion in at least the direction indicated by M1 in FIG. 10C.

Figure 11:
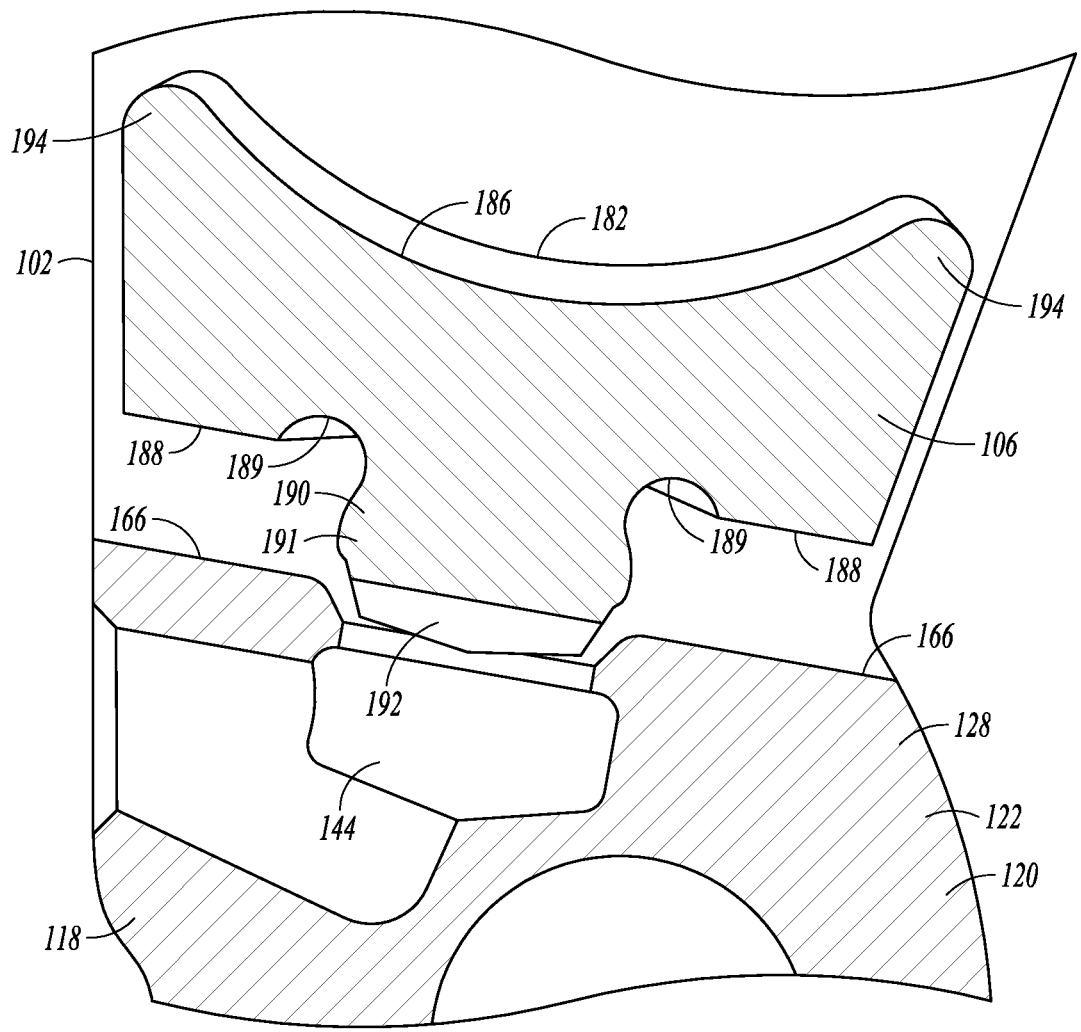
FIG. 11 is a cross-sectional view of a portion of the humeral component and the humeral bearing of the elbow prosthesis prior to coupling the humeral bearing to the humeral component.

FIG. 11 is a cross-sectional view of a portion of the humeral component 102 and the humeral bearing 106, prior to securing or attaching the humeral bearing 106 to the humeral component 102. Specifically, FIG. 11 shows the base 128 of the yoke 122, including the seating surface 166 and the recess 144, and a portion of the stem 118 and the flange 120 of the humeral component 102. The humeral bearing 106 can be configured to attach to the base 128 of the yoke 122. As described above in reference to FIG. 7, the humeral bearing 106 can include the seating surface 188 and the peg 190. The peg 190 can be generally circular shaped, and the collar portion 191 of the peg 190 can have a larger diameter than a base portion 192.

In an example, the recess 144 in the base 128 can be a generally circular shaped recess. In certain examples, the recess 144 can have a non-circular shape and the peg 190 can have a non-circular shape.

Figure 12:
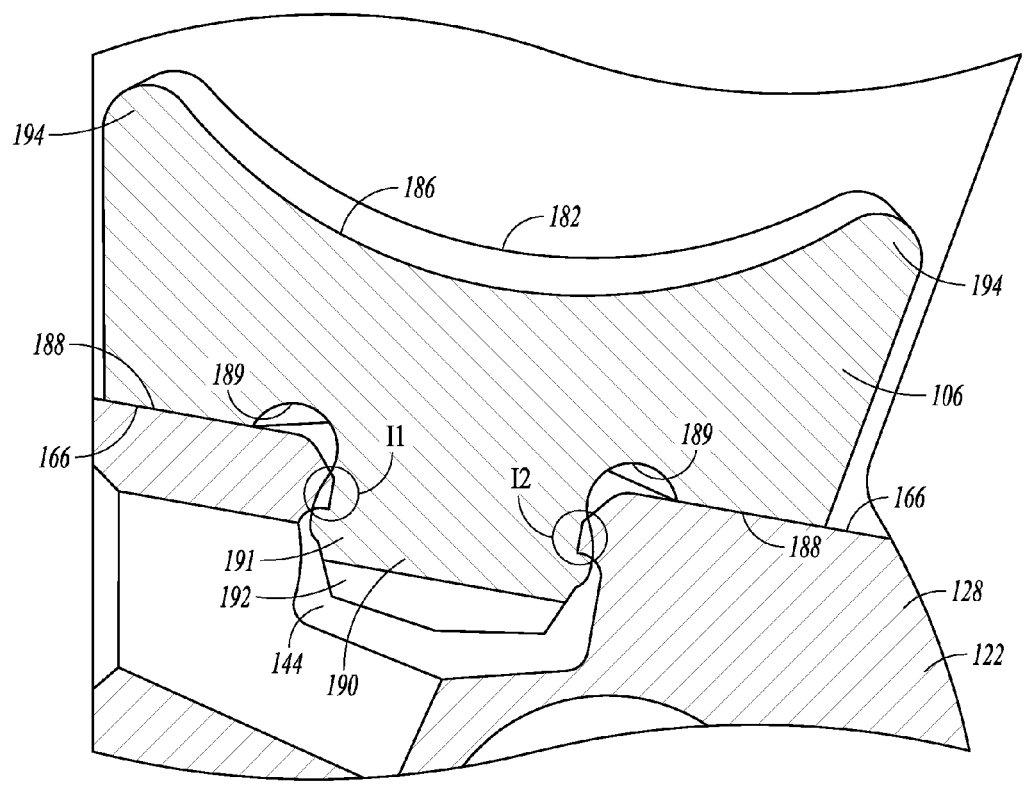
FIG. 12 is a cross-sectional view showing the humeral bearing coupled to the humeral component.

FIG. 12 shows the humeral component 102 and the humeral bearing 106 as the humeral bearing 106 is secured to the humeral component 102, such as by securing the peg 190 in the recess 144.

In an example, the peg 190 can be inserted into the recess 144 by applying a force to the humeral bearing 106, such as using a blunt tool that contacts the articulation surface 182 of the humeral bearing 106. The force can be applied until the peg 190 compresses and squeezes through an opening of the recess 144. Once the collar portion 191 is through the opening, the collar portion 191 can relax or spread out within the recess 144. FIG. 12 shows at least one interference I1 and I2 between the collar portion 191 and the walls forming the recess 144. The peg 190 can overcome this generally circumferential interference, such as by the compression of the collar portion 191 as described above. This type of press-fit can promote a secure attachment of the humeral bearing 106 to the humeral component 102 and can limit or resist movement of the humeral bearing 106.

At least one undercut 189 can be included in the seating surface 188 of the humeral component 106 such that the seating surfaces 166 and 188 of the base 128 of the humeral component and the humeral bearing 106, respectively, can contact one another.

Figure 13A:
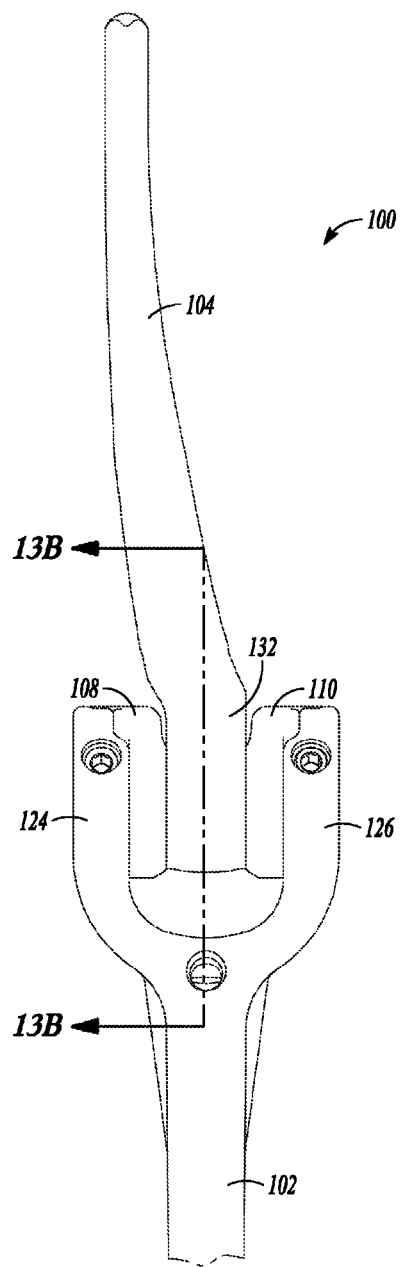
FIG. 13A is a perspective view of a portion of the elbow prosthesis in an assembled state.

FIG. 13A shows the elbow prosthesis 100 in an assembled position and includes the humeral component 102 having the first 124 and second 126 ears, and the ulnar component 104 having the ulnar head 132 shown between the first 108 and second 110 ulnar bearings.

Figure 13B:
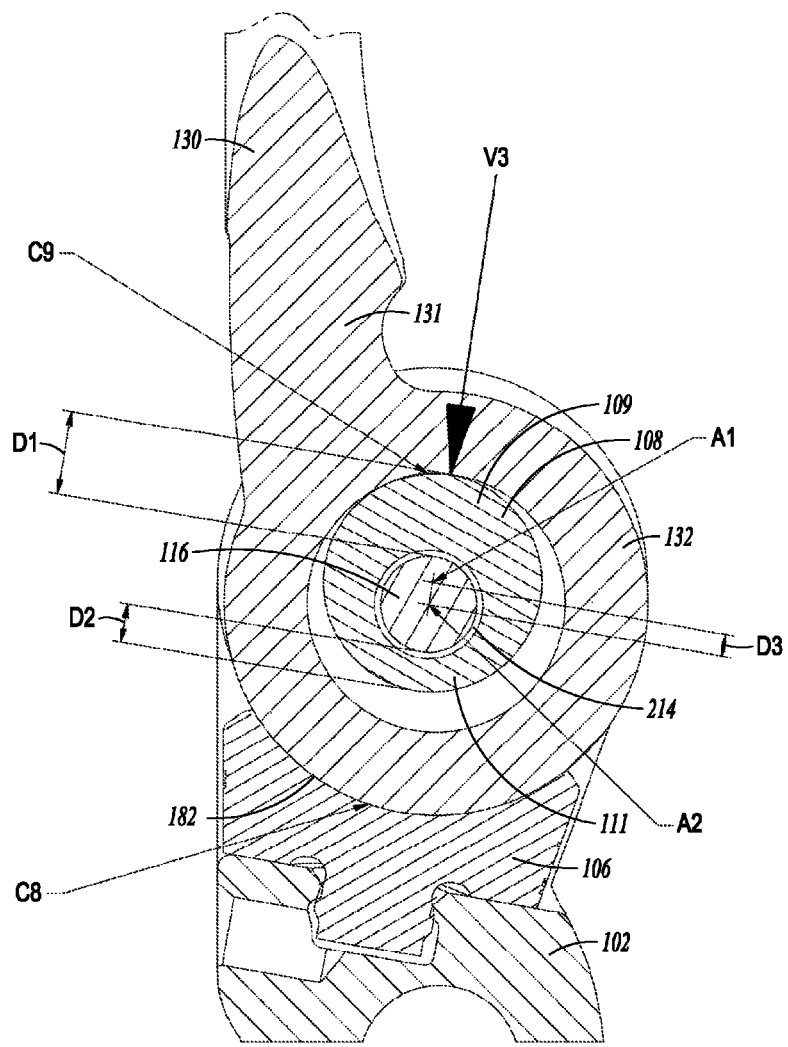
FIG. 13B is a cross-sectional view of a portion of the elbow prosthesis of FIG. 13A.

FIG. 13B is a cross-sectional view of the elbow prosthesis 100 taken along the line 13B-13B in FIG. 13A. FIG. 13B shows an engagement of the ulnar head 132 with the humeral bearing 106 and an engagement of the ulnar head 132 with the first ulnar bearing 108. As the ulnar head 132 articulates, an outer surface of the ulnar head 132 can contact the articulation surface 182 of the humeral bearing 106 in a contact area represented by C8 in FIG. 13B. Over time, surfaces can begin to wear; however, because the humeral bearing 106 can remain substantially stationary, the ulnar head 132 can articulate across the articulation surface 182 and the wear can be spread across a greater area, including the contact area C8.

As described above, the first 108 and second 110 ulnar bearings are press fit onto the pin 116. Thus the ulnar bearings 108 and 110 are substantially stationary within the elbow prosthesis 100. As the ulnar head 132 articulates, an inner surface of the ulnar head 132 can contact an outer surface of the first ulnar bearing 108 in an area represented by C9 in FIG. 13B. As similarly described above in reference to the articulation surface 182 of the humeral bearing 106, wear across the first ulnar bearing 108 can be spread over a greater area, including the contact area C9.

The first ulnar bearing 108 can be configured such that the opening 214 in the ulnar bearing 108 is offset from an axis of the bearing extension 208 (FIG. 8B) of the ulnar bearing 108. Similarly, FIG. 13B shows a bearing axis A1 and a pin axis A2, which can be offset from one another by a distance D3. A lower region 111 of the first ulnar bearing 108 can occupy less space between the bearing extension 208 and the opening 214, as compared to an upper region 109 of the first ulnar bearing 108—this is represented in FIG. 13B by a distance D1 on the upper region 109 being greater than a distance D2 on the lower region 111. This offset can maximize a material thickness between the bearing extension 208 and the opening 214 in a region of the prosthesis that can endure common and high loads during a life of the prosthesis 100. Moreover, the anatomic load or compressive joint load V3 can be shared by a simultaneous contact represented by the contact area C8 between the ulnar head 132 and the humeral bearing 108 and the contact area C9 between the ulnar head 132 and the ulnar bearing 108, thus extending the life of the prosthesis 100 by helping to further reduce bearing wear.

The elbow prosthesis 100 can be configured to include multiple components and features that alone or in combination contribute to a stability of the elbow prosthesis over a life of the prosthesis inside the body of the patient. The various bearings can work in combination with the fasteners and the pin to provide a stable attachment of the ulnar component to the humeral component. The configuration of the bearings can limit or resist micro-motion of the bearings within the elbow prosthesis 100. The bearings can work in combination with the fasteners and the pin of the elbow prosthesis to limit or resist loosening of the fasteners. Multiple points of contact of the fastener and the pin, with one another and with other parts of the elbow prosthesis, can result in a stable design. The configuration of the bearings being substantially fixed or stationary relative to the articulating ulnar head of the ulnar component can minimize wear of the bearing articulation surfaces.

Figure 14:
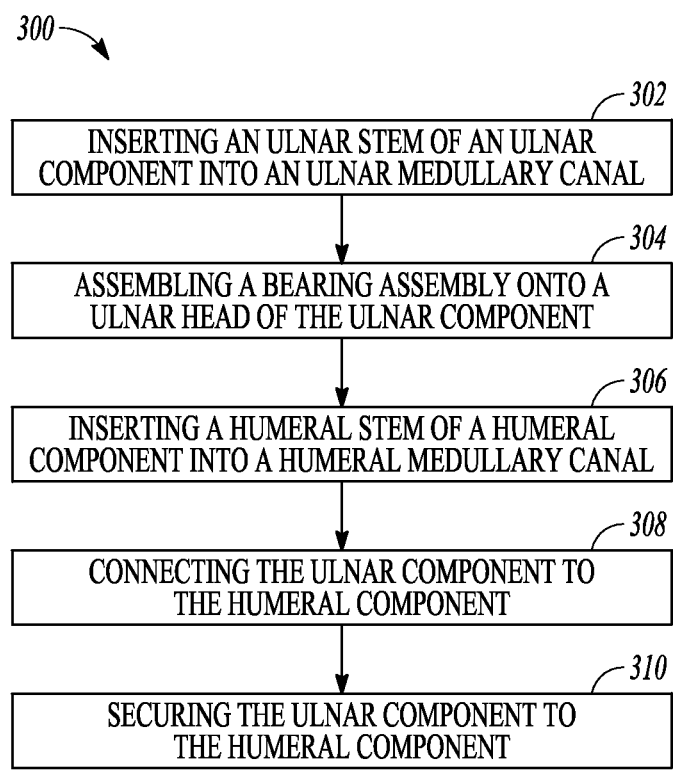
FIG. 14 illustrates a method of repairing an elbow joint of a patient using an elbow prosthesis in accordance with the present patent application.

FIG. 14 illustrates a method 300 of repairing an elbow joint of a patient using a prosthesis, such as an elbow prosthesis as described herein. The elbow prosthesis can include an ulnar component and a humeral component. At 302, a user can insert an ulnar stem of the ulnar component into an ulnar medullary canal of the patient. An ulnar head connected to the ulnar stem can remain exposed outside of the ulnar medullary canal. At 304, the user can assemble a bearing assembly onto the ulnar head. The bearing assembly can include a first ulnar bearing, a second ulnar bearing, and a pin extendable through the first ulnar bearing, the second ulnar bearing, and the ulnar head. At 306, the user can insert a humeral stem of the humeral component into a humeral medullary canal. A yoke connected to the humeral stem can remain exposed outside of the humeral medullary canal. The yoke can include first and second ears extending from a base of the yoke.

At 308, a user can connect the ulnar component to the humeral component. In an example, 308 can include placing a first end portion of the pin of the bearing assembly into an opening in the first ear of the yoke, and placing a second end portion of the pin into an opening in the second ear of the yoke. Connecting the ulnar and humeral components can enable the ulnar component to pivot relative to the humeral component. At 310, a user can secure the ulnar component to the humeral component. In an example, 310 can include threading a first fastener into the first ear of the yoke and a second fastener into the second ear of the yoke. A portion of the first fastener can engage with the first end portion of the pin and a portion of the second fastener can engage with a second end portion of the pin.

In an example, 310 can include securing the first ulnar bearing to the first ear of the yoke and securing the second ulnar bearing to the second ear of the yoke. The first ulnar bearing can include a tab insertable into a recess in the first ear of the yoke. The second ulnar bearing can include a tab insertable into a recess in the second ear of the yoke.

In an example, the method 300 can include securing a humeral bearing into the base of the yoke, prior to connecting the ulnar component to the humeral component. The humeral bearing can include an articulating surface structured to allow articulation of the ulnar head relative to the humeral component.

In certain examples, at least some of the steps of the method 300 can be performed in a different order than what is described above. In certain examples, one or more tools can be used at various steps in the method 300 to assist with an assembly of the elbow prosthesis and/or an implantation of the elbow prosthesis into the body of the patient. In an example, an assembly tool can be used to assemble the bearing assembly onto the ulnar head of the ulnar component. Reference is made to a co-pending application filed the same day as this application, U.S. Ser. No. 13/800,650, entitled "ASSEMBLY TOOL FOR A PROSTHESIS," and directed to an assembly tool configured to assembly the bearing assembly onto the ulnar component. In an example, a tool can be used to secure the humeral bearing into the base of the yoke.

Although specific configurations of an elbow prosthesis are shown in the figures and particularly described above, other designs of an elbow prosthesis can be used. For example, the elbow prosthesis can also be customized for a patient (e.g., provided with at least one patient specific component).

The elbow prosthesis 100 can be provided in combination with an assembly tool such that, for example, a user can have easy access to the assembly tool during an implantation procedure for the elbow prosthesis 100. In an example, a system and/or a kit for repairing an elbow joint of a patient can include the elbow prosthesis 100 and an assembly tool. In an example, the kit can include a plurality of prostheses of varying sizes and/or a plurality of components of varying sizes. The kit can include instructions for use of the assembly tool. In an example, the elbow prosthesis 100 and the assembly tool can be separately provided to the user, but used in combination during the implant procedure. The assembly tool can be reusable in a subsequent implantation procedure after undergoing sterilization.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An elbow prosthesis comprising:
   a humeral component comprising a humeral stem and a yoke having first and second ears extending from a base of the yoke;
   a humeral bearing positionable in the base of the yoke;
   an ulnar component comprising an ulnar stem and an ulnar head;
   a first ulnar bearing positionable between the first ear of the yoke and the ulnar head;
   a second ulnar bearing positionable between the second ear of the yoke and the ulnar head;
   a pin having a first end portion and a second end portion and configured to extend through the ulnar head, the first ulnar bearing and the second ulnar bearing, wherein the first end portion of the pin is configured to extend into a first opening in the first ear of the yoke and the second end portion of the pin is configured to extend into a second opening in the second ear of the yoke, and wherein the ulnar component is configured to pivot about the pin to enable movement of the ulnar component relative to the humeral component;
   a first fastener insertable in a third opening in the first ear of the yoke, the first fastener configured for engaging with the first end portion of the pin;
   a second fastener insertable in a fourth opening in the second ear of the yoke, the second fastener configured for engaging with the second end portion of the pin;
   wherein the first fastener is a first screw having a threaded portion, a conical portion and an end portion, and the second fastener is a second screw having a threaded portion, a conical portion and an end portion.

2. The elbow prosthesis of claim 1 wherein the first and second openings in the first and second ears of the yoke, respectively, are generally V-shaped and the first and second end portions of the pin each have at least two points of contact with the first and second openings, respectively.

3. The elbow prosthesis of claim 1 wherein the third opening in the first ear of the yoke includes a first threaded bore for engaging with the threaded portion of the first screw, and the fourth opening in the second ear of the yoke includes a second threaded bore for engaging with the threaded portion of the second screw.

4. The elbow prosthesis of claim 1 wherein the third opening in the first ear of the yoke includes a first channel formed in the first ear for receiving the end portion of the first screw, and the fourth opening in the second ear of the yoke includes a second channel formed in the second ear for receiving the end portion of the second screw.

5. The elbow prosthesis of claim 1 wherein the conical portion of the first screw is engagable with a first groove in the first end portion of the pin and the conical portion of the second screw is engageable with a second groove in the second end portion of the pin.

6. The elbow prosthesis of claim 1 wherein the humeral bearing is configured such that the ulnar head articulates against a surface of the humeral bearing when the ulnar component pivots relative to the humeral component.

7. The elbow prosthesis of claim 1 wherein the first ulnar bearing includes a first bearing extension configured to extend into an aperture in the ulnar head and the second ulnar bearing includes a second bearing extension configured to extend into the aperture in the ulnar head, and wherein an end face of the first bearing extension is positionable adjacent to an end face of the second bearing extension.

8. The elbow prosthesis of claim 7 wherein a first opening on the first ulnar bearing is offset from an axis of the first bearing extension and a second opening on the second ulnar bearing is offset from an axis of the second bearing extension.

9. The elbow prosthesis of claim 7 wherein the first bearing extension is configured such that an inner surface of the ulnar head articulates against a surface of the first bearing extension and the second bearing extension is configured such that an inner surface of the ulnar head articulates against a surface of the second bearing extension.

10. The elbow prosthesis of claim 1 wherein an external face of the first ulnar bearing is configured to contact the first ear of the yoke and an external face of the second ulnar bearing is configured to contact the second ear of the yoke.

11. The elbow prosthesis of claim 10 wherein the first ulnar bearing comprises a first tab extending from the external face and configured to press fit into a recess in the first ear of the yoke, and the second ulnar bearing comprises a second tab extending from the external face and configured to press fit into a recess in the second ear of the yoke.

12. The elbow prosthesis of claim 1 wherein the humeral bearing includes a peg extending from a bottom surface of the humeral bearing, the peg being configured for press fit engagement with a recess in the base of the yoke.

13. An elbow prosthesis comprising:
    a humeral component comprising a humeral stem and a yoke having first and second ears extending from a base of the yoke, wherein each of the first and second ears has a threaded bore;
    an ulnar component comprising an ulnar stem and an ulnar head;
    an ulnar bearing assembly structured to engage the ulnar head;
    a pin configured to extend through the ulnar head and the bearing assembly, the pin having a first end portion positionable within a first opening in the first ear of the yoke and a second end portion positionable within a second opening in the second ear of the yoke, wherein the ulnar component is configured to pivot about the pin to enable movement of the ulnar component relative to the humeral component;
    a first screw having a threaded head configured to be received within the threaded bore of the first ear, the first screw further including a non-threaded portion configured to engage with the first end portion of the pin; and
    a second screw having a threaded head configured to be received within the threaded bore of the second ear, the second screw further including a non-threaded portion configured to engage with the second end portion of the pin.

14. The elbow prosthesis of claim 13 further comprising a humeral bearing positionable in the base of the yoke, wherein the ulnar head is configured to articulate against a surface of the humeral bearing when the ulnar component pivots relative to the humeral component.

15. The elbow prosthesis of claim 14 wherein the humeral bearing includes a peg extending from a bottom surface of the humeral bearing and configured to engage with a recess in the base of the yoke.

16. The elbow prosthesis of claim 13 wherein the bearing assembly comprises a first bearing having an external face engageable with the first ear of the yoke and a second bearing having an external face engageable with the second ear of the yoke.

17. The elbow prosthesis of claim 16 wherein an axis of the first and second bearings is offset from an axis of the pin.

18. The elbow prosthesis of claim 16 wherein the first bearing includes a first bearing extension configured to extend into an aperture in the ulnar head and the second bearing includes a second bearing extension configured to extend into an aperture in the ulnar head, and wherein an end face of the first bearing extension is positionable adjacent to an end face of the second bearing extension.

19. The elbow prosthesis of claim 18 wherein the end face of the first bearing extension includes a first compression rib and the end face of the second bearing extension includes a second compression rib.

20. The elbow prosthesis of claim 13 wherein the non-threaded portion of the first screw is tapered and engageable with a first groove in the first end portion of the pin and the non-threaded portion of the second screw is tapered and engageable with a second groove in the second end portion of the pin.

21. The elbow prosthesis of claim 20 wherein the first and second openings in the first and second ears of the yoke are generally V-shaped and form first and second seats, and the first and second end portions of the pin have at least two points of contact each with the first and second seats, respectively.

22. The elbow prosthesis of claim 21 wherein the first screw is configured to apply a load to the pin to secure the pin within the first seat and the second screw is configured to apply a load to the pin to secure the pin within the second seat.

* * * * *

UNITED STATES PATENT AND TRADEMARK OFFICE
CERTIFICATE OF CORRECTION

PATENT NO. : 8,936,647 B2
APPLICATION NO. : 13/800567
DATED : January 20, 2015
INVENTOR(S) : Wagner et al.

It is certified that error appears in the above-identified patent and that said Letters Patent is hereby corrected as shown below:

On the Title page, Item (72), column 1, line 5, delete "Chururbusco" and insert --Churubusco--, therefor In the Claims Column 5, line 58, Claim 5, delete "engagable" and insert --engageable--, therefor Signed and Sealed this
Twenty-sixth Day of May, 2015

Michelle K. Lee
*Director of the United States Patent and Trademark Office*